US011058093B2

(12) United States Patent
Guo et al.

(10) Patent No.: US 11,058,093 B2
(45) Date of Patent: Jul. 13, 2021

(54) SYSTEMS AND METHODS FOR MONITORING AND CONTROLLING DROSOPHILA ACTIVITY

(71) Applicant: BRANDEIS UNIVERSITY, Waltham, MA (US)

(72) Inventors: Fang Guo, Waltham, MA (US); Hyung-jae Jung, Ann Arbor, MI (US); Michael Rosbash, Newton, MA (US)

(73) Assignee: BRANDEIS UNIVERSITY, Waltham, MA (US)

( * ) Notice: Subject to any disclaimer, the term of this patent is extended or adjusted under 35 U.S.C. 154(b) by 288 days.

(21) Appl. No.: 15/771,844

(22) PCT Filed: Oct. 31, 2016

(86) PCT No.: PCT/US2016/059639
§ 371 (c)(1),
(2) Date: Apr. 27, 2018

(87) PCT Pub. No.: WO2017/075563
PCT Pub. Date: May 4, 2017

(65) Prior Publication Data
US 2018/0310521 A1    Nov. 1, 2018

Related U.S. Application Data

(60) Provisional application No. 62/249,160, filed on Oct. 30, 2015.

(51) Int. Cl.
*A01K 1/03* (2006.01)
*A01K 67/033* (2006.01)
(Continued)

(52) U.S. Cl.
CPC ............ *A01K 1/031* (2013.01); *A01K 29/005* (2013.01); *A01K 67/033* (2013.01); *G01N 21/6486* (2013.01); *A01K 1/0047* (2013.01)

(58) Field of Classification Search
CPC ..... A01K 1/031; A01K 1/0047; A01K 29/005
See application file for complete search history.

(56) References Cited

U.S. PATENT DOCUMENTS 4,548,804 A * 10/1985 Williamson ........... G01N 33/48
119/6.5
6,806,954 B2 * 10/2004 Sandstrom ......... G01N 21/6456
250/458.1
(Continued)

FOREIGN PATENT DOCUMENTS

CN    101869093         5/2012
CN    101869093 B  *   5/2012   ........... A01K 67/033

OTHER PUBLICATIONS

*Drosophila*, Chinese translation, bab.la, <https://en.bab.la/dictionary/english-chinese/drosophila (Year: 2020).*
(Continued)

*Primary Examiner* — Michael H Wang
(74) *Attorney, Agent, or Firm* — Quarles & Brady LLP

(57) ABSTRACT

Systems and methods for monitoring and controlling activities of *Drosophila* organisms are provided. In one aspect, a method includes acquiring, using a first activity detector, imaging data tracking movements of the *Drosophila* organisms, and acquiring, using a second activity detector, bioluminescence data corresponding to a neural activity of the *Drosophila* organisms. The method also includes correlating, using the acquired data, a behavioral activity and neural activity of the *Drosophila* organisms, and determining, using the correlation, an activity profile for the *Drosophila* organisms. The method further includes providing, based on the activity profile, a stimulation to the *Drosophila* organisms to control at least one of the behavior activity or the neural activity over a time period extendible to a nominal life cycle of the *Drosophila* organisms.

16 Claims, 33 Drawing Sheets

(51) Int. Cl.
  *A01K 29/00*   (2006.01)
  *G01N 21/64*   (2006.01)
  *A01K 1/00*    (2006.01)

(56) References Cited

U.S. PATENT DOCUMENTS

| | | | | |
|---|---|---|---|---|
| 6,860,152 | B2* | 3/2005 | Lund | G01M 7/06 |
| | | | | 73/663 |
| 6,977,722 | B2* | 12/2005 | Wohlstadter | G01N 21/69 |
| | | | | 356/246 |
| 7,199,378 | B2* | 4/2007 | Ishiura | G01N 21/763 |
| | | | | 250/461.2 |
| 8,263,821 | B2* | 9/2012 | Brulet | A01K 67/0275 |
| | | | | 800/14 |
| 2004/0232351 | A1 | 11/2004 | Ishiura et al. | |
| 2005/0273867 | A1 | 12/2005 | Brulet et al. | |
| 2008/0153928 | A1* | 6/2008 | van Ravenzwaay | A01K 29/00 |
| | | | | 514/789 |
| 2012/0189549 | A1* | 7/2012 | Claridge-Chang | |
| | | | | A01K 67/033 |
| | | | | 424/9.2 |
| 2013/0116065 | A1* | 5/2013 | Yamamoto | A63B 53/04 |
| | | | | 473/345 |
| 2016/0326219 | A1* | 11/2016 | Riedler | C12Q 1/485 |
| 2018/0055434 | A1* | 3/2018 | Cheung | G09B 5/065 |

OTHER PUBLICATIONS

Imafuku, Michio and Takashi Haramura, 2011, Zoological Society of Japan, Zoological Science, 28(3), 195-198 (Year: 2011).*
International Search Report and Written Opinion for International Patent Application No. PCT/US2016/059639 dated Jan. 6, 2017.

* cited by examiner

SYSTEMS AND METHODS FOR MONITORING AND CONTROLLING DROSOPHILA ACTIVITY

CROSS-REFERENCE TO RELATED APPLICATIONS

The present application represents the U.S. National Stage of International Application No. PCT/US2016/059639, filed Oct. 31, 2016 which is based on, and incorporates herein, it its entirety, U.S. Provisional Patent Application No. 62/249,160 filed on Oct. 30, 2015 and entitled "SYSTEMS AND METHODS FOR MONITORING AND CONTROLLING DROSOPHILA ACTIVITY."

BACKGROUND

The present disclosure is directed to monitoring and controlling activities of small animals. More particularly, the present disclosure is directed to monitoring and controlling the activities of Drosophila, and other organisms.

Animal models are often used to provide insight into the molecular and cellular mechanisms associated with human disease, as well as help develop various treatment strategies. In particular, Drosophila flies are one of the most studied organisms in biological research, particularly in the field of genetics and developmental biology. The low overhead cost, ease of care, and minimal equipment requirements makes Drosophila organisms an ideal model for a variety of research and clinical applications, including, physiology, aging, toxicity, pharmacology, drug screening, just to name a few.

Studies involving small organisms have included a variety of behavioral, locomotor and cognitive assays. Existing techniques for investigating multiple Drosophila organisms have utilized various activity monitors fitted with one or more cameras, capable of tracking their movements and behavior patterns in up to three dimensions. For example, Inan et al. ("A portable system for monitoring the behavioral activity of Drosophila, Journal of Neuroscience Methods, 202, 2011) describe a common Drosophila activity monitor ("DAM"). Although some improvements in the sensitivity and accuracy of Drosophila assays have been achieved, many DAMs are designed to track only a few organisms at a time, and can include several complex and expensive components. Also, many such previous systems are limited to tracking over short time periods of time, at most up to just a few hours. Moreover, common DAM can lack sensitivity to tiny movements, and include many blind spots. These present severe technological limitations for applications requiring high-throughput and statistical power, such as drug screening, longevity and aging studies, and so forth.

In light of the above, there is a need for improved systems and methods for monitoring, as well as controlling, the activities of small organisms, such as Drosophila flies.

SUMMARY

The present disclosure overcomes the drawbacks of previous technologies by providing systems and methods for monitoring and controlling activities of organisms, such as Drosophila flies. Embodiments described herein include a number of features and capabilities, including the ability to provide organism activity information in real-time and over extended time periods, not obtainable using previous technologies. For instance, in some aspects, activity profiles may be determined using behavior and neural activity measured over periods up to several weeks. In addition, the present disclosure allows for controlling organism activities using various stimulations and environmental conditions.

In one aspect of the present disclosure, a system for monitoring activities of Drosophila organisms is provided. The system includes an organism holder comprising a plurality of chambers configured for holding Drosophila organisms therein, a first activity detector configured to acquire imaging data tracking movements of the Drosophila organisms, and a second activity detector configured to acquire bioluminescence data corresponding to a neural activity of the Drosophila organisms. The system also includes a processor configured to receive imaging data and bioluminescence data acquired over a time period extendible to a nominal life cycle of the Drosophila organisms, and correlate, using the received data, a behavioral activity and neural activity of the Drosophila organisms. The processor is also configured to determine, using the correlation, an activity profile for the Drosophila organisms, and generate, using the activity profile, a report indicative of a condition of the Drosophila organisms over the time period. The system further includes an output for displaying the report.

In another aspect of the disclosure, a method for controlling activities of Drosophila organisms is provided. The method includes acquiring, using a first activity detector, imaging data tracking movements of the Drosophila organisms, and acquiring, using a second activity detector, bioluminescence data corresponding to a neural activity of the Drosophila organisms. The method also includes correlating, using the acquired data, a behavioral activity and neural activity of the Drosophila organisms, and determining, using the correlation, an activity profile for the Drosophila organisms. The method further includes providing, based on the activity profile, a stimulation to the Drosophila organisms to control at least one of the behavior activity or the neural activity over a time period extendible to a nominal life cycle of the Drosophila organisms.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The present invention will hereafter be described with reference to the accompanying drawings, wherein like reference numerals denote like elements. The patent or application file contains at least one drawing executed in color. Copies of this patent or patent application publication with color drawing(s) will be provided by the Office upon request and payment of the necessary fee.

DETAILED DESCRIPTION

The present disclosure is directed to monitoring and controlling organisms. Specifically, the present disclosure describes various embodiments that provide enhanced capabilities for tracking and controlling multiple small organisms, such as *Drosophila* organisms, with high consistency and throughput. For instance, using systems and methods described herein, the behavioral, neural, locomotor, cognitive, and other activities, of various organisms may be monitored in real-time and up to the end of their nominal life expectancy, providing information not obtainable or considered possible by using previous technologies. For example, long-term measurements of behavior or locomotor activity can be used to identify sleep-wake patterns or circadian cycles in *Drosophila* organisms, as well as analyze courtship and aggression. In addition, systems and methods provided herein may also be used to modify, or maintain, organism activities by controlling environmental conditions experienced by the organisms or by applying various stimulations to the organisms. For example, an optogenetic stimulation may be applied to *Drosophila* organisms to control neural activities within discrete neurons.

In some implementations, information obtained from different measured activities may be combined to characterize the organisms. For instance, video or imaging data showing behavior, locomotion or movement, may be correlated to neural data to determine an activity profile for one or more organisms. Herein, neural data may be generally understood to include data associated with measured neural activity, as well as neuronal activity. In some aspects, neural data may be in the form of bioluminescence data indicative of various processes of interest, such as transcriptional activities, neural or neuronal activations, and so forth. Herein, bioluminescence may also encompass biofluorescence or biophosphorescence. As an example, bioluminescence data may reflect the presence of calcium, CaLexA, CaLexA-LUC and other targets.

As will be appreciated from descriptions below, the present systems and methods may find use in a variety of applications, including applications for drug development, longevity or aging studies, genetic and mutant screenings, disease investigations, and so forth.

Figure 1:
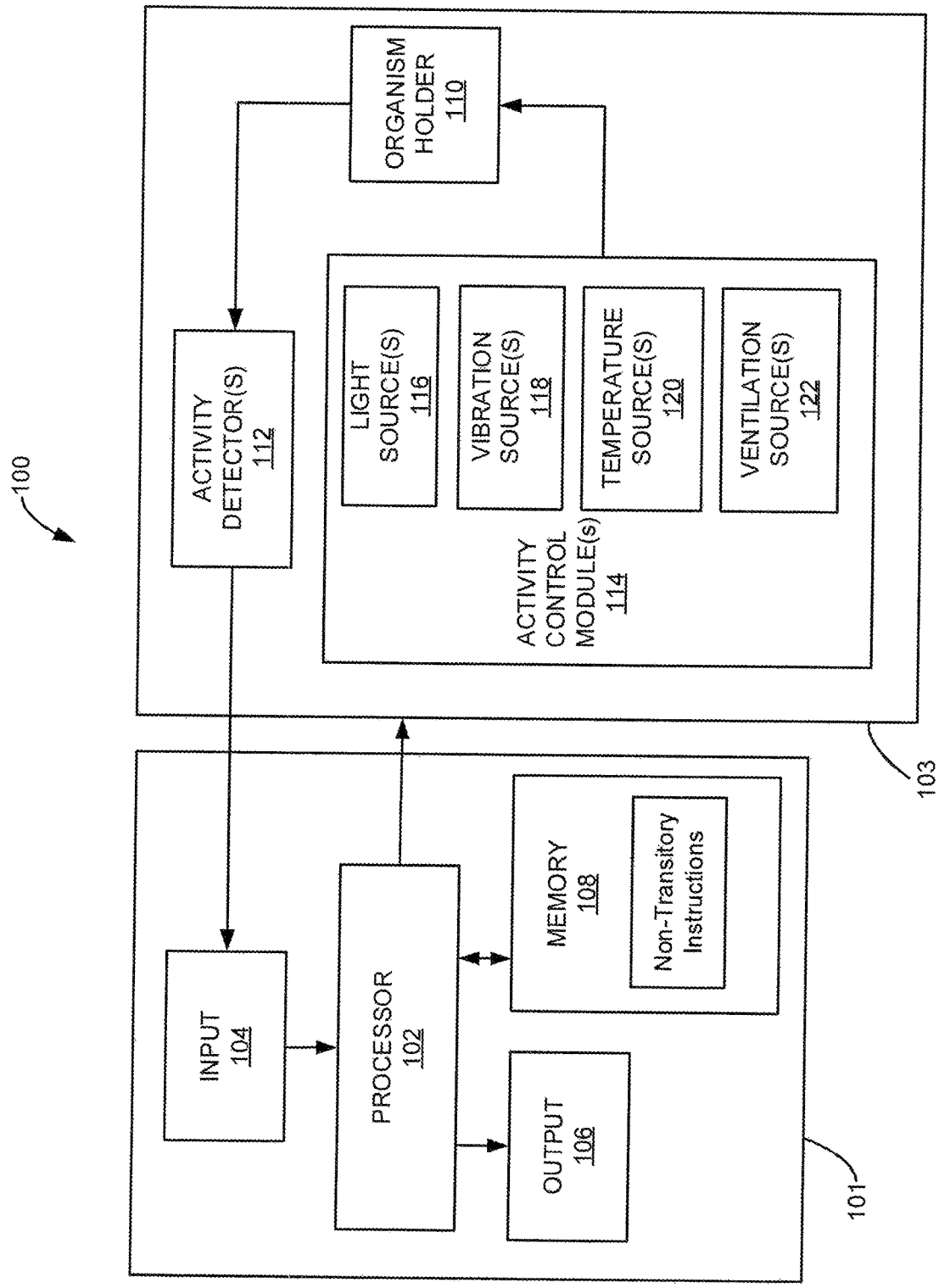
FIG. 1 shows a schematic diagram of an example system for monitoring and/or controlling small organisms, in accordance with aspects of the present disclosure.

Turning now to FIG. 1, an example system 100 for monitoring and controlling small organisms, such as *Drosophila* organisms, is shown. As shown, the system 100 may generally include a controller 101 and an organism assembly 103. The controller 101 may include a processor 102, an input 104, an output 104, and a memory 106. The organism assembly 103 may include an organism holder 110, as well as one or more activity detectors 112 and activity control modules 114 in communication with the controller 101.

The controller 101 may be any computing device, apparatus or system configured in accordance with aspects of the present disclosure. For instance, the system 100 may be a personal computer, workstation, and the like. In some implementations, the system 100 may be a portable device, such as a laptop, tablet, smartphone, or other portable device or apparatus. In addition, the system 100 may operate as part of, or in collaboration with a computer, system, device, machine, mainframe, or server. In this regard, the system 100 may be any system, designed to integrate with a variety of software and hardware capabilities and functionalities, and may be capable of operating autonomously or semi-autonomously.

The input 104 of the controller 101 may be configured to receive a variety of information or data, and communicate with any system, device, or apparatus, as well as a data storage, memory, or database, using a wired or wireless communication connection, such Bluetooth, WiFi or other communication protocol. As shown in FIG. 1, in some aspects, the input 104 may be configured to receive information and data from the one or more activity detectors 112. For example, the input 104 may receive imaging or video data, or bioluminescence data captured using one or more cameras. In addition, the input 104 may include a flash-drive, CD or DVD drive, or other computer-readable medium receptacle. The input 104 may also include various input elements, such as a mouse, keyboard, touchpad, touch screen, buttons, and the like, configured to receive indications or selections from a user.

The processor 102, in addition to being configured to operate the system 100, may also be configured to carry out non-transitory instructions stored in the memory 108 for monitoring and controlling organism activities, such as activities of *Drosophila* organisms, in accordance with the present disclosure. Specifically, the processor 102 may be configured to control acquisition of data either intermittently or continuously. For example, the processor 102 may control the activity detector(s) 112, which may include one or more cameras, to acquire data over a time period that can extend to a nominal life cycle of the organisms being monitored. As such, the activity detectors(s) may be configured to acquire and possibly store a large amount of data. Alternatively, such data may be stored in the memory 108 or other data storage location. In some implementations, the activity detector(s) 112 may include on or more filters.

In some aspects, the processor 102 may communicate with a microcontroller, such as an Arduino board, Raspberry Pi, and the like, that is configured to control the activity detector(s) 112. In some aspects, the processor 102 may store to and retrieve data from the memory 108 or other data storage location.

The processor 102 may also be configured to receive and process the acquired or accessed data to generate various information associated with the monitored organisms. In some aspects, the processor 102 may be configured to correlate different data, such as data associated with behavioral and neural activity. The processor 102 may then determine various activity profiles for the organisms, and generate various information based on the determined activity profiles. For example, the processor 102 may generate information indicative of a condition or activity of the analyzed organisms, such as movement patterns, sleep patterns, wake patterns, circadian cycles, and so on.

In some aspects, the processor 102 may communicate with the activity control module(s) 114 or other hardware to apply stimulations or control conditions experienced by the organisms. For example, the processor 102 may communicate with an Arduino board to control the timing, frequency, wavelength, and intensity of an optogenetic stimulation delivered to the organisms using a light source. In this manner, a neural activity of *Drosophila* organisms may be controlled or modified using the optogenetic stimulation, for example. Similarly, the processor 102 may control the behavior, wake or sleep pattern of the organisms by controlling light, temperature, vibration, and so forth.

The processor 102 may then be configured to generate a report in any form. The report may provide various information or data, and be provided to a user using output 106, and/or stored in memory 108. For example, the report may provide real-time imaging of the organisms, tracked movements, and so forth.

With reference to the organism assembly 103, the organism holder 110 may include multiple individual chambers or wells, arranged in any configuration, with each chamber shaped and dimensioned as desired and configured to accommodate one or more organisms. In one example, the organism holder 110 may include a 96-well plate. In some configurations, the organism holder 110 may be scalable, using multiple chamber units that can be connected or assembled together. For example, an organism holder 110 may include four chamber units, each unit being a 96-well plate.

Such scalable organism holder 110 provides flexibility for monitoring a large number of organisms, as well as different organism groups, concurrently under similar conditions, such as lighting, temperature, ventilation and so forth. This may be advantageous in applications requiring reproducibility, high-throughput, and parallel processing. For example, in one application, sleep deprivation, learning, and memory studies may be investigated in *Drosophila* organisms using a single 96-well plate. In a drug screening application, for example, organisms with different characteristics or genotypes may be monitored concurrently. For instance, different organism groups, each potentially housed in a separate unit, as described above, and each group having received different drugs, drug variants, or drug doses, may be monitored concurrently.

As described, in some applications, organisms may be monitored for an extended period of time, such as up to their nominal life cycle, using the system 100. As such, the organism holder 110 may include sufficient amount of nourishment for sustaining the organism for such period of time. For example, *Drosophila melanogaster*, herein referred to as *Drosophila* organisms, may be monitored for a time period that extends up to 4 weeks. As such, the organism holder 110 may include nourishment, such as sucrose, and agar, to allow *Drosophila* organisms to live for several weeks. By way of example, approximately 300 microliter ("μL") of nourishment may be included in a 96-well plate, although it may be appreciated that the amount may vary depending on the particular application. In some aspects, the holder 110 may be configured so as to permit access or replenishment of nourishment without interfering with acquisition of the imaging data and bioluminescence data, as will be described, such that monitoring can be performed over a time period extendible to or beyond a nominal life cycle of the *Drosophila* organisms.

The activity detector(s) 112 may be configured to detect the activity of the monitored organisms, including tracking movements or behavioral activity of organisms housed in the organism holder 110. As such, the activity detector(s) 112 may include one or more cameras for acquiring video or imaging data, continuously or intermittently, and in substantially real-time. In some aspects, the activity detector(s) 112 may include capabilities for enhancing, or filtering the acquired imaging data. In addition, the activity detector(s) 112 may also be configured to acquire bioluminescence data indicative of neural or neuronal activity of the organisms. As such, the activity detector(s) 112 may include one or more bioluminescence plate readers or other bioluminescence detectors.

As shown in FIG. 1, the organism assembly 103 may also include one or more activity control modules 114 configured to provide stimulation or control conditions experienced by the organisms. For instance, stimulation may be in the form of light, vibration, electricity, and so on. Conditions may include temperature, ventilation, gas, liquid, as well as chemical environments experienced by the organisms. As such, the activity control module 114 may include one or more light source(s) 116, vibration source(s) 118, temperature source(s) 120, ventilation source(s) 122, and others.

In particular, the light source(s) 116 may be utilized for imaging purposes, as well as for controlling the level and type of illumination, or light stimulation, experienced by the organisms. The light provided by the light source(s) 116 may be focused or diffuse, and have timing, duration, frequency, wavelength, and intensity that can vary according to a specific application. In addition, light may be provided from various directions. In one embodiment, the light source(s) 116 can include one or more light emitting diodes ("LEDs") or LED strips configured to provide light with wavelengths approximately between 400 and 900 nm, although other values may be possible. In some embodiments, the light source(s) 116 may produce white light that is filtered using various color filters. In one example application, 627 nm LED light may be utilized to provide optogenetic stimulation to *Drosophila* organisms expressing CalexA-LUC or CsChrimson, where Chrimson is a type of channelrhodopsin. Flies with different channelrhodopsins can be activated using different wavelengths. In another example application, white light may be used to entrain *Drosophila* flies to specific circadian rhythms.

Vibration may also be used to control the behavioral activities of the monitored organisms. For example, inducing sleep deprivation and arousal using vibration may allow sleep/wake patterns of the organisms to be controlled. As such, one or more vibration source 118 configured to induce or transmit vibrations to the organism holder 110 may be included in the organism assembly 103. In some implementations, the vibration source(s) 118 may include a solenoid (for example, as shown in FIG. 2C) or other mechanism connected mechanically to the organism holder 110.

Other elements capable of stimulating the organisms may also be included in the organism assembly 103, as shown in FIG. 1. For instance, one or more temperature source(s) 120 may be utilized to control the temperature experienced by the organisms. Also, one or more ventilation source(s) 122 may be utilized to control the ventilation or gas atmosphere experienced by the organisms. Other activity control modules 114 may also include electrical sources, gas sources, chemical sources, and so forth. In addition, the organism assembly 103 may include other hardware, such as data acquisition or control hardware (not shown in FIG. 1), in communication with the activity detectors 112 and activity control modules 114. For example, organism assembly 103 may include an Arduino Uno board, a Raspberry Pi board, and the like, as well as other circuitry. Alternatively, such hardware may be included in the controller 101. Although the controller 101 and organism assembly 103 are shown in FIG. 1 as separate, it may be appreciated that these, or various components therein, may be integrated into one apparatus or system.

In some embodiments, the organism assembly 103 may include a housing, an enclosure, a support assembly, as well as various supporting structures. The configuration of the organism assembly 103 may vary, being adapted to specific applications and components utilized, as described above. For example, in applications requiring specific lighting conditions, the organism assembly 103 may include a light-tight enclosure. Also, in applications requiring specific ambient gas/liquid conditions, the organism assembly 103 may include a gas or liquid-tight enclosure. In applications where portability or compactness is advantageous, the organism assembly 103 may be configured with appropriate weight and dimensions.

Figure 2A:
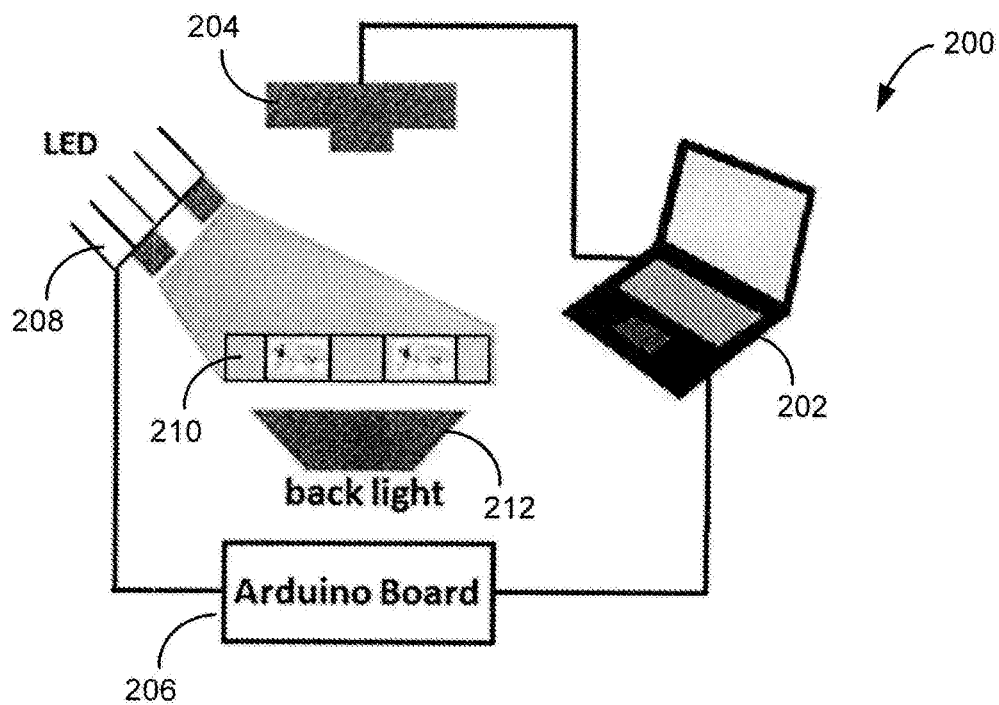
FIG. 2A shows one embodiment of the example system shown in FIG. 1.

By way of example, FIG. 2A shows one non-limiting embodiment of the system 100 described above. The organism system 200 includes a computing device 202 in communication with a camera 204 and a controller board 206. As shown, the controller board 206 may include an Arduino board. The controller board 206 is in communication with a front light source 208 oriented towards an organism holder 210. The organism system 200 also includes a back light source 212, as shown. In particular, the controller board 206 may be configured to control the timing, during, frequency, wavelength, and intensity of illumination delivered to the organisms housed in the organism holder 208, while the camera 204 is configured to track behavior and other activities of the organisms. In some aspects, activities may monitored up to the nominal life cycle of the organisms.

Figure 2B:
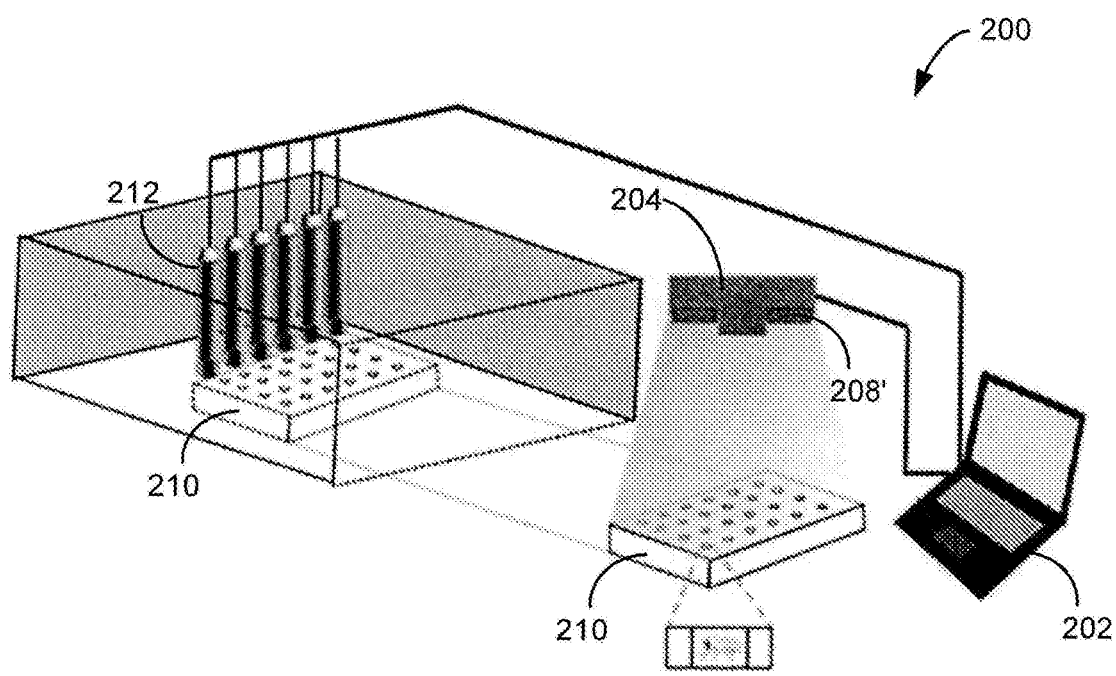
FIG. 2B shows another embodiment of the example system shown in FIG. 1.
Figure 2C:
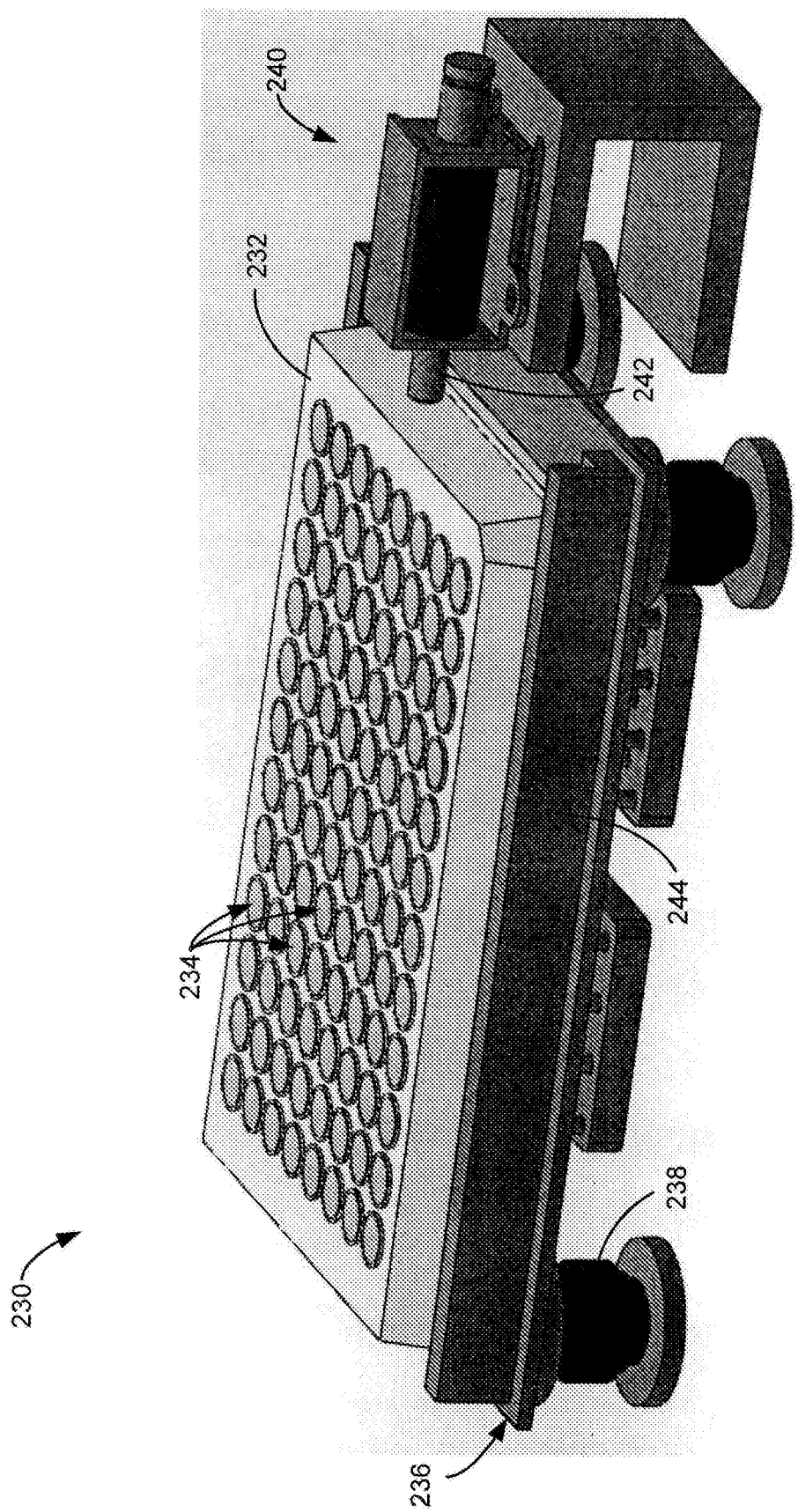
FIG. 2C shows a perspective view of an example organism holder, in accordance with aspects of the present disclosure.

Another non-limiting embodiment of the system 100 is shown in FIG. 2B. In addition to a computing device 202, camera 204, controller board 206 (not shown in FIG. 2B), front light camera 208', and organism holder 210, the organism system 200 also includes additional detectors 212 in communication with the computing device 202. In some aspects, the detectors 212 are configured to acquire bioluminescence data. As shown in FIG. 2B, the organism holder 210 may be displaced between positions facing the detectors 212 and camera 204. The displacement may be achieved manually, or automatically as directed by the computing device 202 and/or controller board 206. Hence, the organism system 200 may therefore include additional components not shown in FIG. 2B, such various motors, gears and other mechanical components, as well as other hardware configured for achieving such displacement.

By way of example, FIG. 2C shows one embodiment of an organism holder, as described with reference to FIG. 1. In particular, the organism holder 230 may include a rectangular chamber unit 232 having a number of organism wells 234. For example, the chamber unit 232 can be a 96-well plate. The chamber unit 232 rests on a base 236, which is elevated by four vibration isolation supports 238. As shown, the chamber unit 232 is coupled to a solenoid 240 using a mechanical coupling 242. When the solenoid 240 is activated, mechanical force is transmitted to the chamber unit 232 such that the latter moves along a track defined by guides 244 on the base 236. In this manner, vibration can be applied to the organisms housed in the organism wells 234.

Figure 2D:
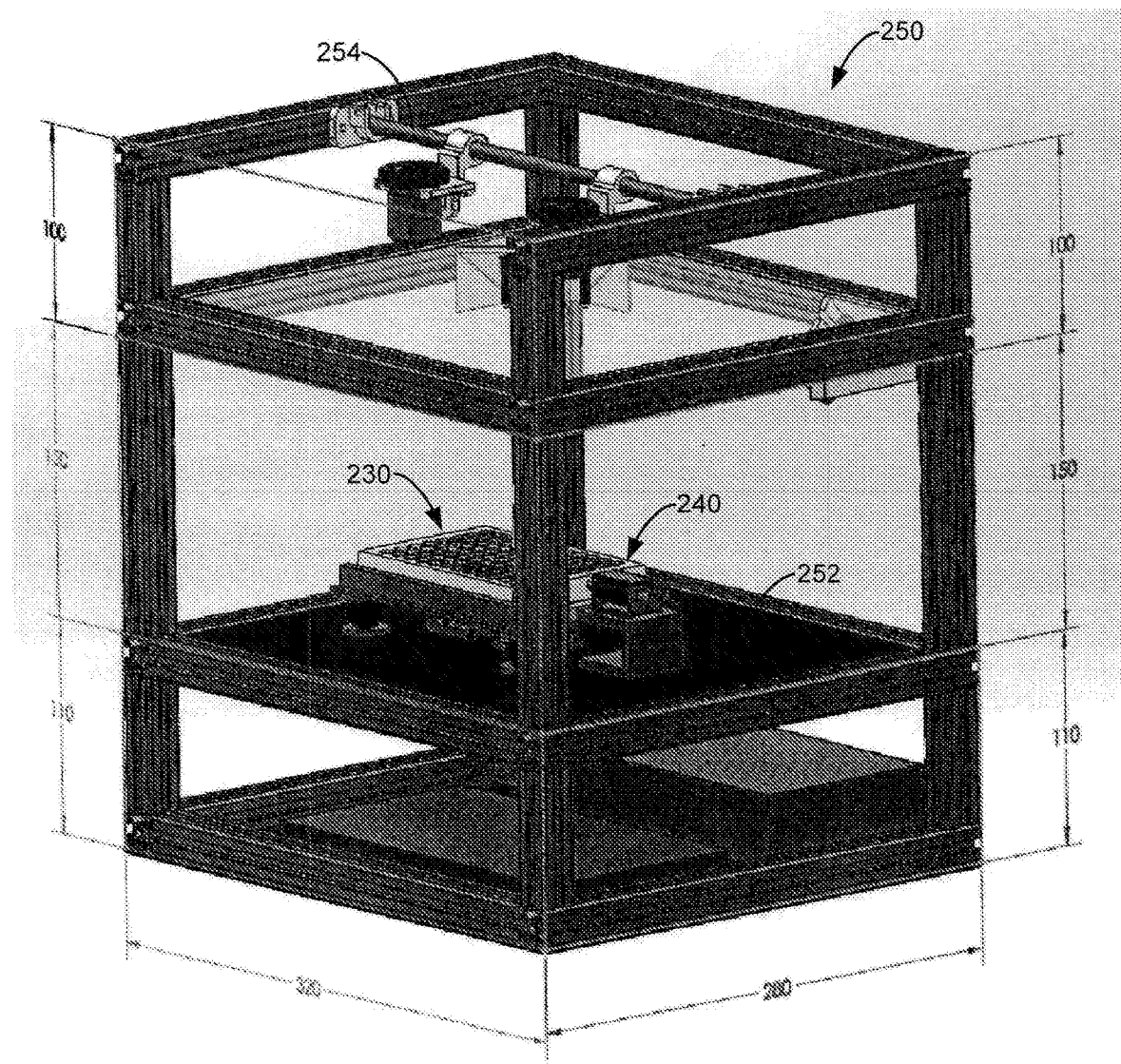
FIG. 2D shows a perspective view of an example support assembly, in accordance with aspects of the present disclosure.

As described with reference to FIG. 1, the organism assembly 103 may include a support assembly. By way of example, FIG. 2D shows one embodiment of a support assembly 250. As shown, the support assembly 250 includes a support platform 252 for holding an organism holder 230 and solenoid 240. The support assembly 250 also includes at least one fixed or movable support beam 254 extending across the top of the support assembly 250 and configured to hold various components, including activity detectors, light sources, cameras, and so on, in various positions and orientations. Alternatively, or additionally, other portions of the support assembly 250 may be configured to hold one or more of these various components. These components may be held using various fasters, couplings or brackets. In some desirable configurations, such components would arranged in a manner to achieve optimal performance without any mutual interference. For example, LEDs can positioned along the support beam 254, or other locations on the support assembly 250, and oriented to allow for even illumination of the organism holder 230. Similarly, a camera may be positioned and oriented to obtain a full view of the entire organism holder 230, or a portion thereof. In some embodiments, the support assembly 250 may be constructed using modular components, so that a variety of configurations may be obtained.

Figure 2G:
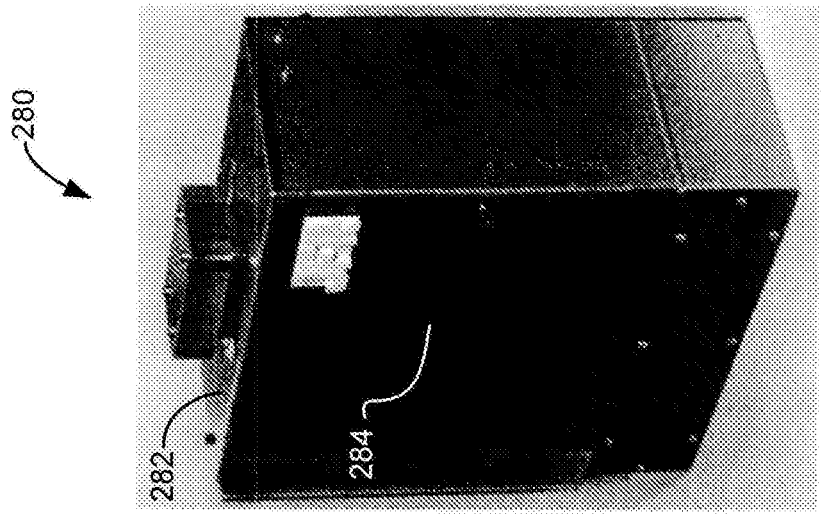
FIG. 2G shows a perspective view of the embodiment shown in FIG. 2E.
Figure 2F:
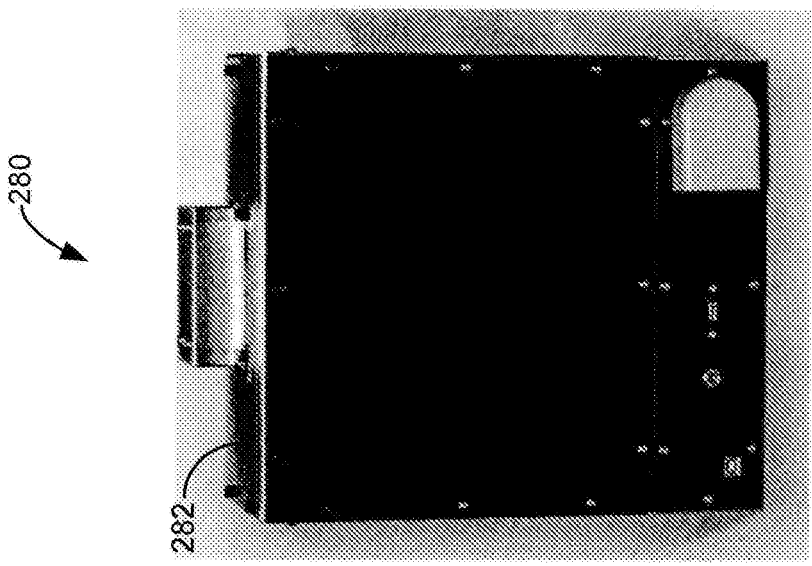
FIG. 2F shows a back view of the embodiment shown in FIG. 2E.
Figure 2E:
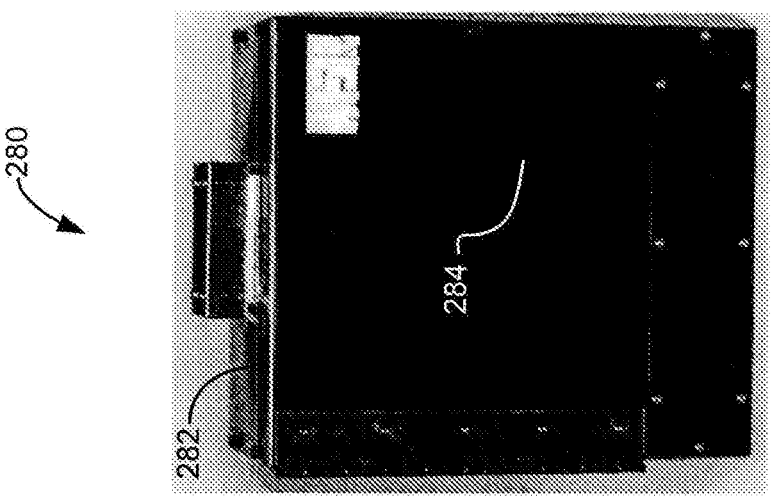
FIG. 2E shows a front view of yet another embodiment of the example system shown in FIG. 1.
Figure 2H:
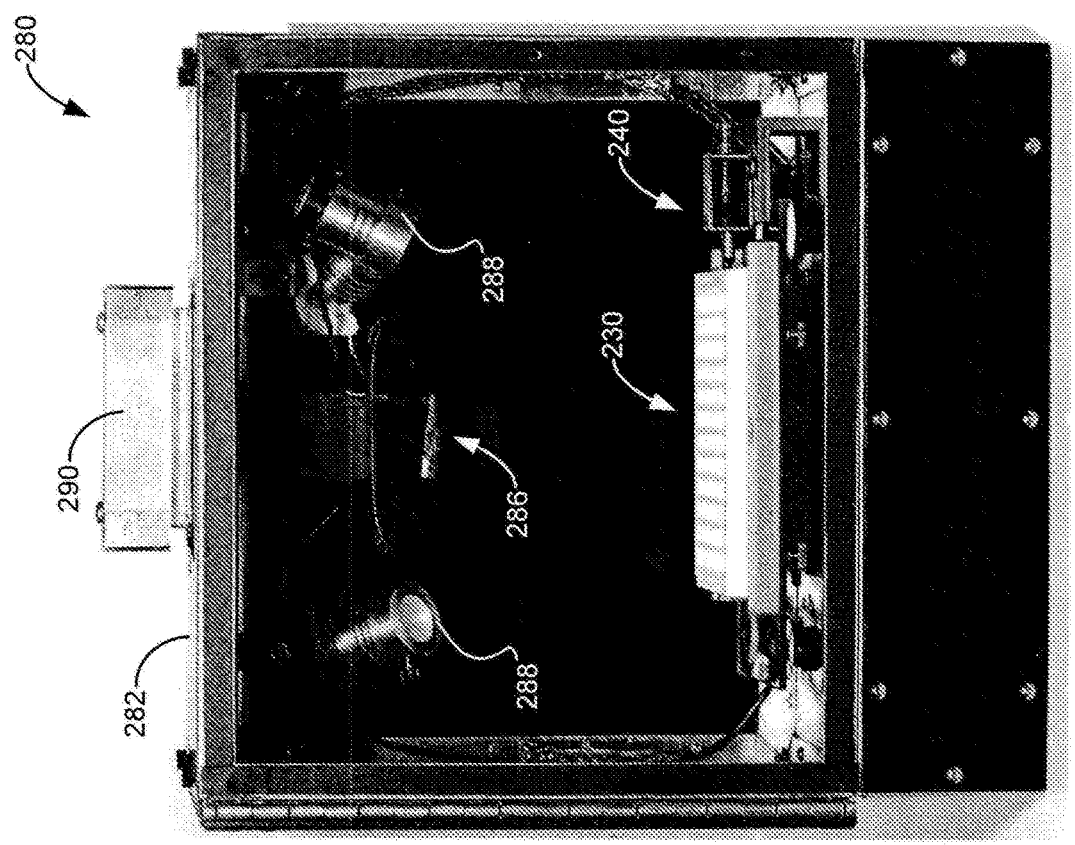
FIG. 2H shows another front view of the embodiment shown in FIG. 2E.

Referring now to FIGS. 2E-2H another embodiment of a system, as described with reference to FIG. 1, is illustrated. In particular, FIGS. 2E-2G show a front, back and perspective view, respectively, of an organism assembly 280 having a light-tight enclosure 282. The enclosure 282 may have various designs and be constructed using various materials, including thin aluminum as shown, as well as plastics, such as acrylonitrile butadiene styrene ("ABS"), or acrylics. The enclosure 282 includes a cover 284 that can be removed, or opened, as shown in FIG. 2H. Inside the enclosure 282, a number of components can be found, including an organism holder 230, a solenoid 240, a camera 286, and LEDs 288, or alternatively LED strips. In particular, the LEDs 288 or LED strips may be interchangeable and directly provide white light, as well as other colors. Alternatively, or additionally, a number of filters may be included with the LEDs 288 or LED strips, or the camera 286, or both. Example filters can include short-pass filters (for example approximately 435 nm cutoff), long-pass filters (for example approximately 850 nm cutoff), ultra-violet filters, infrared filters, various visible light filters (for example, red, blue, green), and filters for other portions or bands of the light spectrum. By way of example, the red LEDs may equipped with filters that block any wavelength above approximately 609 nm. Selection of appropriate filtering may depend upon the particular application. In some aspects, the LEDs 288 or LED strips may include diffusers for providing even illumination.

In some implementations, the organism assembly 280 also includes a back light source that is located below the organism holder 230, as shown in FIG. 2A. The back light source may include one or more infrared LEDs and a diffuser plate for even illumination (not shown in FIG. 2H). In one example, the LEDs may generate infrared light, which could provide night vision that would allow continuous recording of the organisms, day and night. To this end, the organism holder 230 may be constructed using transparent, semi-transparent or opaque materials that selectively allowing specific light therethrough.

The organism assembly 280 also includes a removable top cover 290 configured to allow ventilation to be connected to the enclosure 282, as well as other inputs. Ventilation may be additionally, or alternatively, provided through the bottom of the organism assembly 280 using a light-tight vent. As organism assembly 280 may also include a number of feedthroughs, for connecting the solenoid 240, camera 286, and LEDs 288 to, a controller or other hardware. Advantageously, such feedthroughs are also light-tight, in order to prevent ambient light from entering the enclosure 282 while in use.

Figure 3:
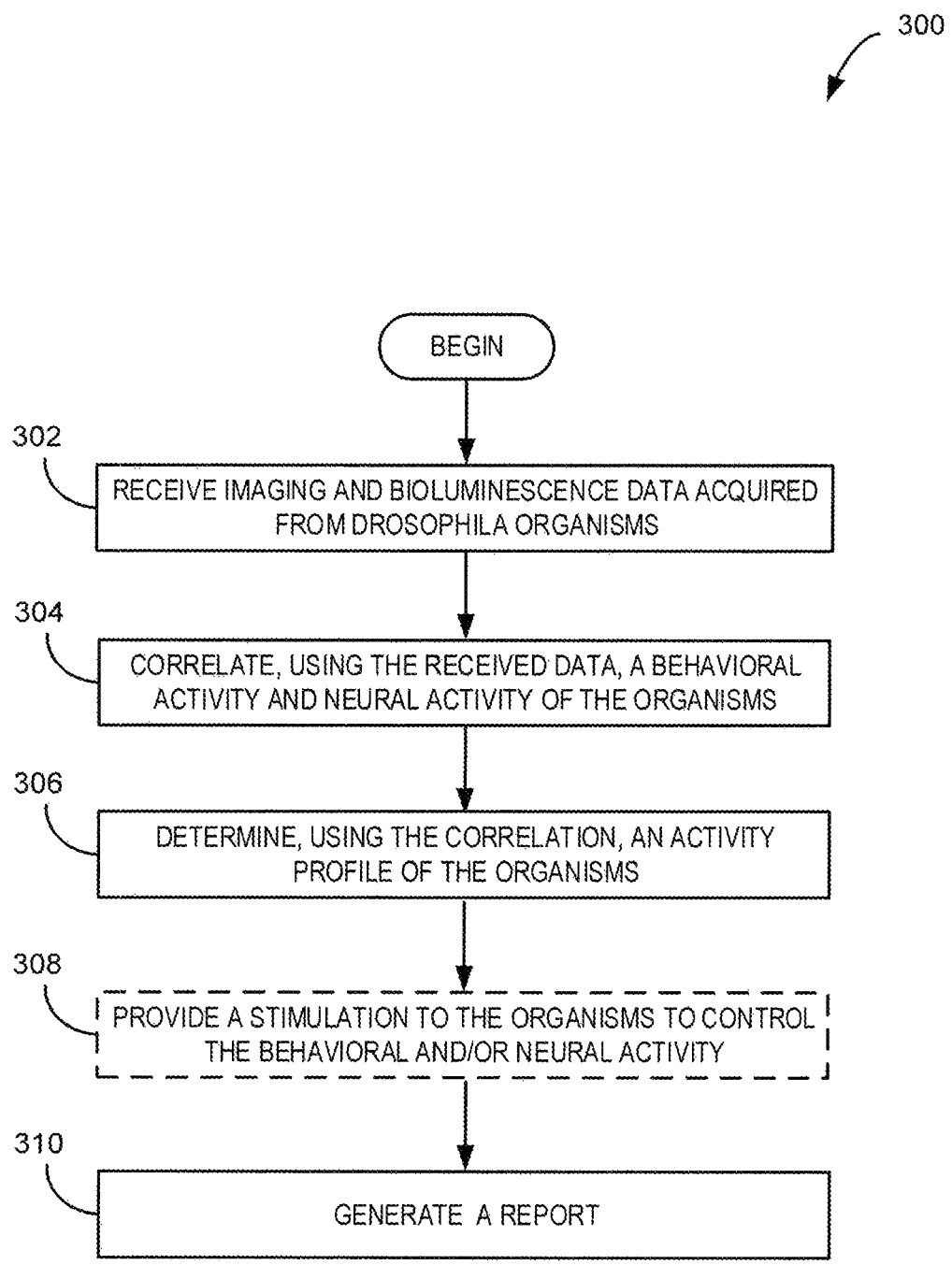
FIG. 3 shows a flowchart setting forth steps of a process in accordance with aspects of the present disclosure.

Turning now to FIG. 3, a flowchart is shown setting forth steps of a process 300 for monitoring and/or controlling activities of organisms, in accordance with aspects of the present disclosure. In some aspects, the process 300 may be carried out using the systems described with reference to FIGS. 1 and 2.

The process 300 may begin with receiving imaging and bioluminescence data and other information corresponding to organisms, such as *Drosophila* organisms, as indicated by process block 302. In particular, the received data may be associated with a number of organisms either described by a single genotype, or multiple genotypes. In some aspects, the data, and other information may be acquired at process block 302, using various activity detectors and inputs. For instance, imaging data tracking movements of the organisms may be acquired using a first activity detector, such as a camera. In addition, bioluminescence data corresponding to a neural activity of the organisms may be acquired using a second activity detector. Advantageously, activity data may be acquired over a time period extendible to a nominal life cycle. For example, in the case *Drosophila* organisms, data acquisition may be extended for up to 4 weeks, or more.

In some aspects, as indicated by process block 304, acquired data and other information may be processed and analyzed to determine various activities of the organisms. For instance, video imaging data may be processed to determine a behavioral or locomotor activity of the organisms. Similarly, bioluminescence data may be processed to determine a neural activity, as well as a gene expression of the organisms. In some aspects, various activities, such as behavioral activity and neural activity, may be correlated, as indicated by process block 304. Then, at process block 306, an activity profile for the organisms may be determined.

In some implementations, a stimulation may be provided to the organisms, as indicated by process block 308, using light, temperature, vibration, electricity, sound, or other method. As described, such stimulation may be used to control behavior, locomotion, gene expression, neural activities, or other activities of the organisms. For instance, an optogenetic stimulation may be provided using one or more LEDs to modifying the neural activity of the *Drosophila* organisms. In some aspects, optogenetic stimulation may target specific neurons in the organism's brain. Also, in some aspects, a modified activity profile may be determined following such stimulation by acquiring and analyzing additional data or information, as described above.

Then at process block 310, a report of any form may then be generated. For example, the report may provide real-time imaging of the organisms, as well as information associated with a conditions of the organisms, behavior and neural activities, and so forth. For example, such information may include sleep patterns, wake patterns, movement patterns, gene expression, locomotion patterns, as well as information related to Circadian cycles, courtship, aggression, and so forth. In some aspects, the report may indicate various correlations between behavior, locomotion, gene expression, neural activity and so forth. In addition, in some aspects, an effectiveness of an administered chemical or pharmaceutical may be included in the report.

The above-described systems and methods may be further understood by way of example. The example is offered for illustrative purposes only, and is not intended to limit the scope of the present invention in any way. Indeed various modifications in addition to those shown and described herein will become apparent to those skilled in the art from the foregoing descriptions and the following example, and fall within the scope of the appended claims.

Example

The Drosophila sleep/wake pattern is sexually dimorphic and sensitive to temperature, with a greatly enhanced midday siesta in males and at higher temperatures. Although little is known about the cellular control of siesta, optogenetic activation of the DN1s, Circadian neurons that promote morning activity, also promotes the siesta. A novel assay tracking the neuronal activity of discrete neurons in wake-behaving flies over multiple days is provided described herein, indicating that DN1 daytime activity is much higher in males than in females. As will be described, the assay simultaneously monitored behavior and indicated that higher temperatures increase both DN1 activity and the siesta. These neurons contact and inhibit the locomotor activity-promoting evening ("E") circadian neurons. Glutamate release from DN1s and the metabotropic glutamate receptor ("mGluRA") in E cells contribute to this inhibition. Circadian modulation of gene expression can explains how the DN1s perform multiple behavioral roles, namely by functionally interacting with different elements of circadian circuitry at different times of day.

Eukaryotic circadian clocks organize a substantial fraction of biochemistry, physiology, endocrinology and even behavior so that specific functions occur preferentially at defined times of day. Much of this circadian output regulation is transcriptional, and it is now estimated that as much as 50% of the mammalian genome is under clock control. The 24 hr timekeeper is also believed to be substantially transcriptional, as many key clock genes and proteins are transcription factors. Some of them inhibit their own transcription, and this negative feedback loop mechanism affects a large number of output genes that are also under clock control. This mechanism as well as many clock genes are conserved between flies and mammals, indicating inheritance from a common ancestor 600 million years ago.

In mammals, these feedback loops take place in many cells and tissues all over the body, including most prominently the approximately 10,000 neurons of the master pacemaker in the hypothalamus, the supra-chiasmatic nucleus ("SCN"). Equivalently, the central circadian region of Drosophila contains about 75 pairs of neurons on each side of the fly brain. They are arranged in about 7 groups, each of which contains 4-30 neurons. Circadian neurons of Drosophila play a major role in determining its characteristic locomotor activity and sleep program. This includes bimodal activity under standard 12:12 light:dark ("LD") conditions, the morning ("M") and evening ("E") anticipation peaks, as well as a siesta during mid-day and quite consolidated sleep at night.

Figure 10:
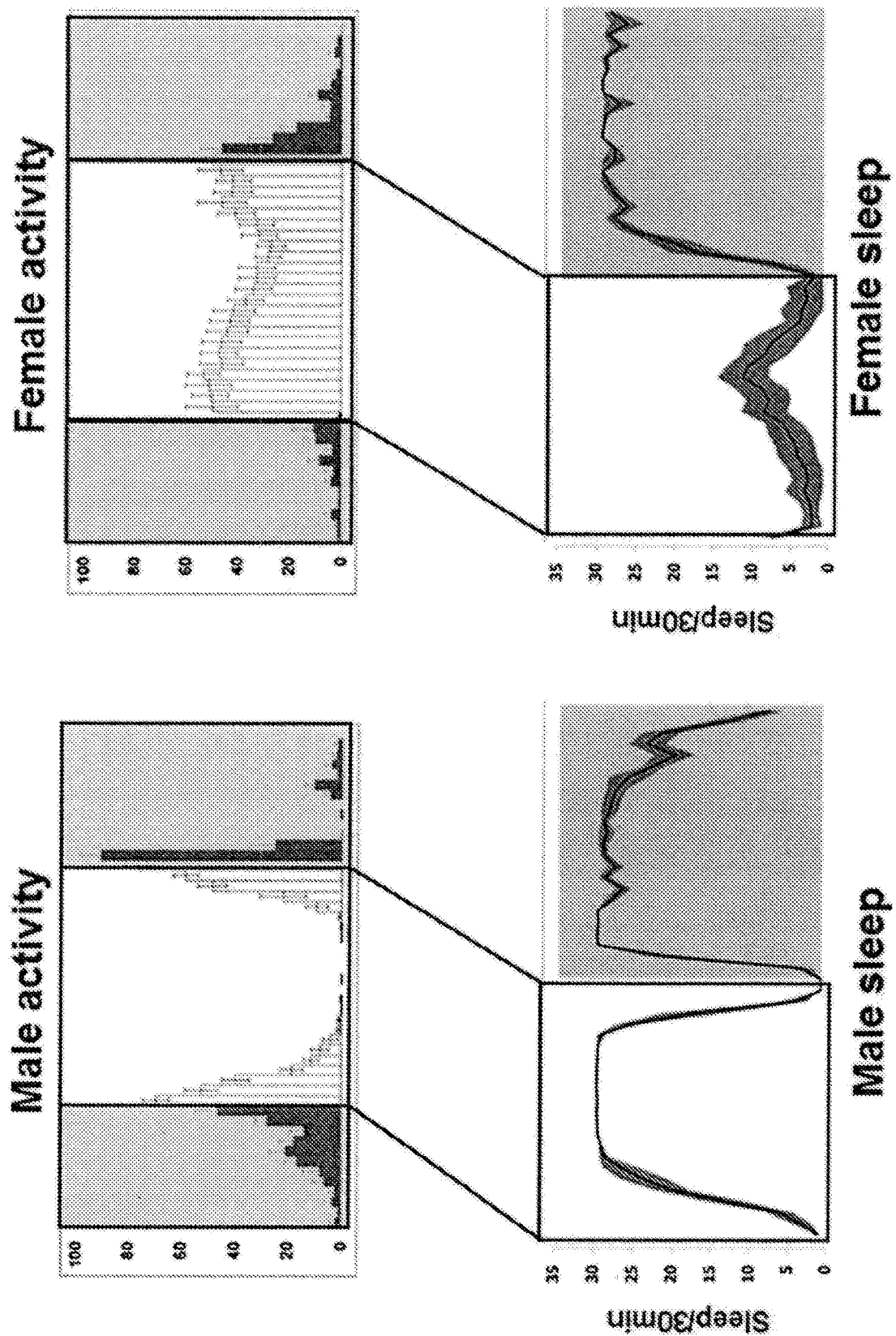
FIG. 10 are graphs illustrating sexual dimorphism of locomotor activity and sleep.

These patterns can be substantially different between males and females. Specifically, males exhibit morning ("M") activity followed by a strong siesta, which is followed by robust evening ("E") activity. In contrast, females show very little M activity before the lights-on event (FIG. 10). They also manifest a fairly constant high activity level during the daytime and as a consequence a quite modest siesta. This also affects E activity, as it is less distinct in females than in males due to the higher levels of preceding activity (FIG. 10). Although there is no explanation for such sexual dimorphism, nor for the cellular control of siesta, other aspects of the sleep/activity program have been linked to specific circadian neurons. For example, a small neuronal group (E cells) including CRY-positive dorsal lateral neurons ("LNds") and the 5th sLNv dictates E activity. Another defined group includes the 4 PDF-positive small ventrolateral neurons ("sLNvs") and determines morning ("M") activity in LD as well as the clock pace in DD (constant darkness).

These sLNvs (also called PDF neurons or M cells) carry out some of their functions through their connections to other circadian neurons. For example, sLNv cell bodies are located in the lateral region of the brain and send prominent axonal projections to the dorsal region, where they contact processes from the dorsally located DN1s. Consistent with this anatomical relationship, DN1s—like sLNvs—have been shown to contribute to the morning activity peak. This is thought to occur via PDF signals from the sLNvs to the PDF receptor ("PDFR") present on the DN1s. These neurons also bridge the connection between the sLNvs and downstream locomotor activity centers, either through neural connections to DH44-positive PI neurons or through release of activity-promoting neuropeptides like DH31. However, wild-type female flies show very little morning activity and yet contain DN1 cells that have an anatomical relationship to PDF neurons that is at least superficially indistinguishable from wild-type male flies. Furthermore, both males and females have robust 24 hr circadian rhythms in DD, making the sLNvs a somewhat less likely candidate for the sexual dimorphism of the siesta and E peak. The fact that differences between sexes are only prominent in LD also suggests that they are more likely linked to circadian neurons downstream from the central timekeepers. This makes the DN1s good candidates for investigation. Specifically, because DN1s may carry out this function through interactions with other circadian neurons, and because E cells complement PDF neurons as the other prominent activity-promoting circadian cell group, a possible connection between DN1s and E cells in addition to the established DN1-M cell connection was considered herein.

Consistent with this hypothesis, blocking DN1 neuronal activity attenuated the male specific activity pattern in LD without disrupting DD rhythmicity. This not only reduced the M peak in males, but also had a strong inhibitory effect on the prominent male siesta. In addition, artificial activation of DN1s enhanced the siesta and even inhibited the onset of the evening activity peak in females. Moreover, male DN1s had a higher excitability than female DN1s during the daytime, which as linked to the gender-dependent siesta levels observed in the two sexes. It was also found that DN1s can dynamically modulate the siesta as well as the subsequent E peak in response to temperature. Anatomical experiments indicated a close connection between DN1s and E cell processes. Additional results indicated that the inhibitory neurotransmitter glutamate from DN1s and the metabotropic glutamate receptor A (mGluRA) in E cells contribute to the DN1 inhibitory effect. Circadian modulation of gene expression added a temporal dimension to the temperature and sex-specific regulation of DN1 activity, explaining how these neurons perform multiple roles, namely, by modulating the strength of functional interactions as a function of time of day.

Method and Materials

Fly Strains

DvPdf-GAL4, Clk4.1m-GAL4, UAS-dTrpA1 (2nd), pdfr5304, UAS-CaLexA, UAS-TNT, UAS-Tet, Pdf-GAL80, UAS-Vglut RNAi (VDRC 202327), UAS-mGluRA RNAi 1 (VDRC 103736), UASmGluRA RNAi 2(VDRC 1793), UAS-CD4::spGFP1-10, LexAop-CD4::spGFP11, 911-QF, LexAop-LUC, Pdfr (R18H11)-GAL4 (48832), Pdfr (R18H11)-LexA (52535), Vglut (R51H05)-GAL4 (41275), Vglut (R51H05)-LexA (54886), UAS-CsChrimson (55136), UAS-Denmark (33064), UAS-Kaede (26161), UAS-syt-GFP (33064), UASKir2.1 (6596), and Tub-GAL80ts (7016) were utilized in the experiments. Flies were reared on standard cornmeal/agar medium supplemented with yeast. The adult flies were entrained in 12:12 light-dark ("LD") cycles at 25° C. The flies carrying GAL4 and UAS-dTrpA1 were maintained at 21° C. to inhibit dTrpA1 activity:

Locomotor Activity and Statistical Analyses

Locomotor activity of individual male flies (aged 3-7 days) was measured with Trikinetics *Drosophila* Activity Monitors (Waltham, Mass.) under 12:12 LD conditions. The activity and sleep analysis was performed with a signal-processing toolbox implemented in MATLAB (MathWorks). Group activity was also generated and analyzed with MATLAB. For dTrpA1-induced neuronal firing experiments, flies were entrained in LD for 3 days at 21° C., transferred to 30° C. for two days, followed by 2 subsequent days at 21° C. All statistical analysis was conducted using IBM SPSS software. The Wilks-Shapiro test was used to determine normality of data. Normally distributed data were analyzed with a two-tailed, unpaired Student t-tests or one way analysis of variance (ANOVA) followed by a Tukey-Kramer HSD Test as the post hoc test. Data were presented as mean behavioral responses, and error bars represent the standard error of the mean ("SEM"). Differences between groups were considered significant if the probability of error was less than 0.05 ($P < 0.05$)

Feeding of Retinal

All trans-retinal powder (Sigma) was dissolved in alcohol to prepare a 100 mM stock solution for CsChrimson experiments. 100 µl stock solution was diluted in 25 ml 5% sucrose and 1% agar medium to prepare 400 µM all trans-retinal (ATR) food. Newly enclosed flies were transferred to ATR food for at least 2 days prior to optogenetic experiments.

Optogenetics and Video Recording System

The behavioral setup for the optogenetics and video recording system is schematized in FIG. 6. Briefly, flies were loaded to white 96-well Microfluor 2 plates (Fisher) containing 5% sucrose and 1% agar food with or without 400 µM ATR. The back light was supplied by an 850 nm LED board (LUXEON) located under the plate. 2 sets of high power LEDs (627 nm) mounted on heat sinks (4 LEDs per heat sink) were symmetrical placed above the plate to provide light stimulation. The angle and height of LEDs was adjusted to allow uniform illumination. The voltage and frequency of red light pulses were controlled by an Arduino UNO board (Smart Projects, Italy). Fly behavior was recorded using a web camera (Logistic C910) without an IR filter. A time-lapse software was used to capture snapshots in 10 second intervals. The LD cycle and temperature was controlled by an incubator and the light intensity was maintained to entrain flies without activating CsChrimson. Fly movement was calculated by Pysolo software and transformed into a MATLAB readable file. The activity and sleep analysis was performed with a signal-processing toolbox implemented in MATLAB (MathWorks) as described above.

In Vivo Luciferase Assays

Figure 5A:
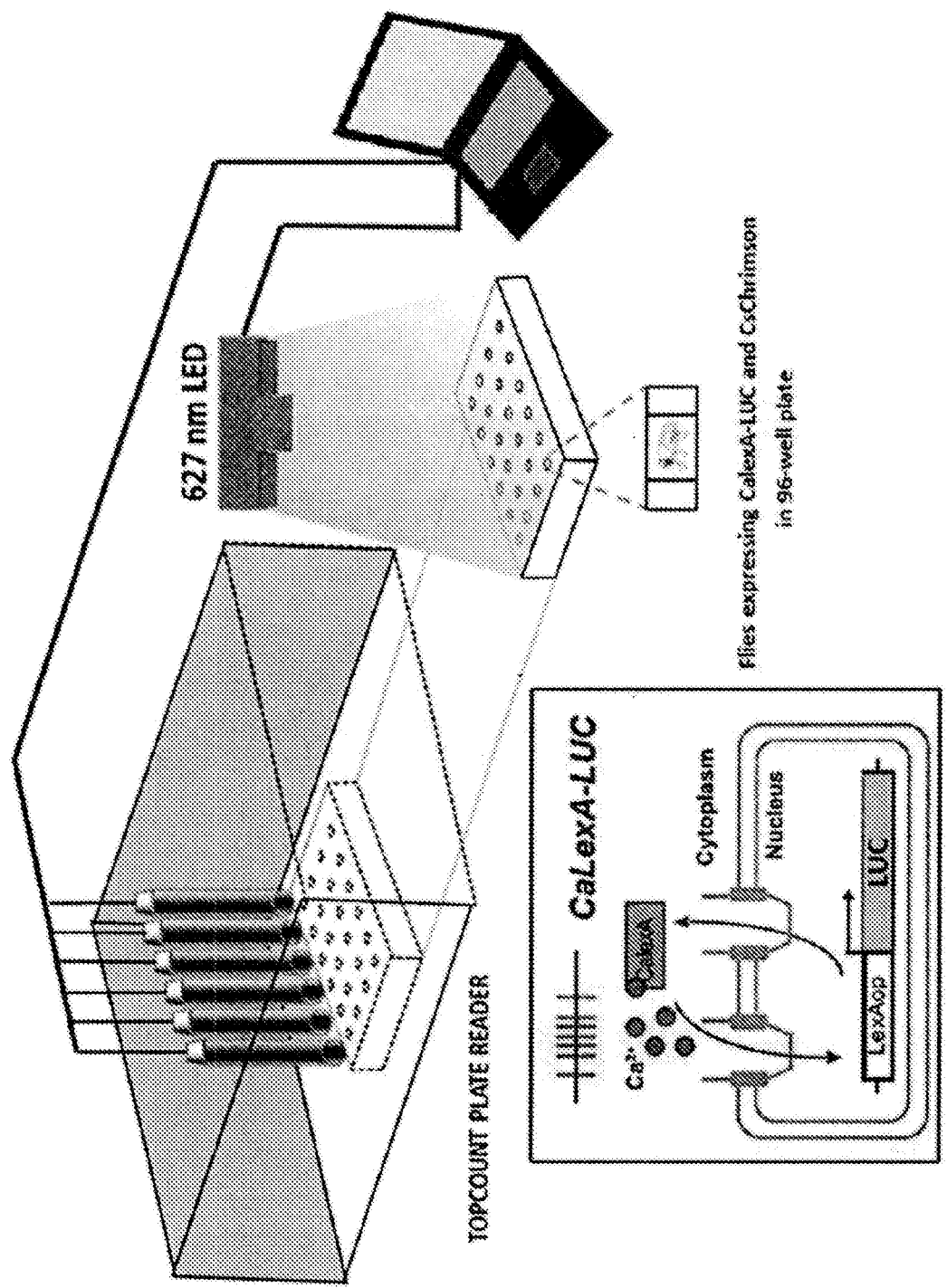
FIG. 5A shows an example configuration for characterizing flies expressing CaLexA-LUC according to the process showed in the boxed panel.

Bioluminescence activity in living flies was measured using previously described protocols. White 96-well Microfluor 2 plates (Fisher) were loaded with 5% sucrose and 1% agar food containing 20 mM D-luciferin potassium salt (GOLDBIO). A 250 µL supply of food was added to each well. Individual male or female flies expressing CaLexA-LUC were first anaesthetized with $CO_2$ and then transferred to the wells. An adhesive transparent seal (TopSeal-A PLUS, Perkin Elmer) was also used to cover the plate, introducing 2-3 holes in the seal to allow for air exchange. Plates were loaded into a stacker in a TopCount NXT luminescence counter (Perkin Elmer). Assays were carried out in an incubator under light:dark conditions. Luminescence counts were collected for 5-7 days. For temperature shift experiments (FIG. 5B), the incubator temperature was set to 23° C. for 3 days and then increased to 30° C. at ZT 0 of the 4th day. Other experiments were performed at 25° C. To combine optogenetic stimulation with the luciferase assays, the stacker was replaced with a customized chamber. 627 nm LEDs mounted to a pair of heat sinks were symmetrically positioned in the chamber to ensure uniform illumination (FIG. 5A). Fly movement in each well was recorded using a web camera attached to the top of chamber. During each hour, the plate sat in the chamber for 55 min and was automatically transferred to the TopCount machine for luminescence reading for 5 min. The raw data was analyzed in MATLAB and with Microsoft Excel. Experiments were repeated at least three times with similar results.

Fly Brain Immunocytochemistry

Immunostaining was performed as described previously. In particular, fly heads were removed and fixed in PBS with 4% paraformaldehyde and 0.008% Triton X-100 for 45-50 min at 4° C. Fixed heads were washed in PBS with 0.5% Triton X-100 and dissected in PBS. The brains were blocked in 10% goat serum (Jackson Immunoresearch, West Grove, Pa.) and subsequently incubated with primary antibodies at 4° C. overnight or longer. For PER and GFP co-staining, a rabbit anti-PER (1:500) and mouse anti-GFP antibody (Invitrogen; 1:1000) were used as primary antibodies. For GRASP staining, a mouse anti-GFP monoclonal antibody (Invitrogen; 1:1000) and a rabbit anti-GFP antibody (Roche; 1:200) were used. After washing with 0.5% PB ST three times, the brains were incubated with Alexa Fluor 633 conjugated anti-rabbit (PER) and Alexa Fluor 488 conjugated anti-mouse (PDF) (Molecular Probes, Carlsbad, Calif.) at 1:500 dilution. The brains were washed three more times before being mounted in Vectashield Mounting Medium (Vector Laboratories, Burlingame, Calif.) and viewed sequentially in 1.1 µm sections on a Leica confocal microscope. To compare the fluorescence signals from different conditions, the laser intensity and other settings were set at the same level during each experiment. Fluorescence signals were quantified by ImageJ as described.

mRNA Profiling from E Cells and DN1s mRNA profiling from E cells and DN1s was performed as previously described. DN1s and E cells were purified from Clk4.1m-Gal4, UAS-EGFP flies (DN1s) and Dv-Pdf-GAL4, UAS-EGFP, PDF-RFP flies, (E cells; GFP+RFP− cells), respectively. Flies were entrained for 3 days and then collected every 4 hours for a total of 6 time points. 2 replicates of 6 time points were performed for each cell type. Sequencing data were aligned to the *Drosophila* genome using Tophat. Gene expression was quantified using the End Sequencing Analysis Tookit (ESAT; http://garberlab.umassmed.edu/software/esat/). ESAT quantifies gene expression only using information from the 3'-end of the gene.

Results

Figure 11:
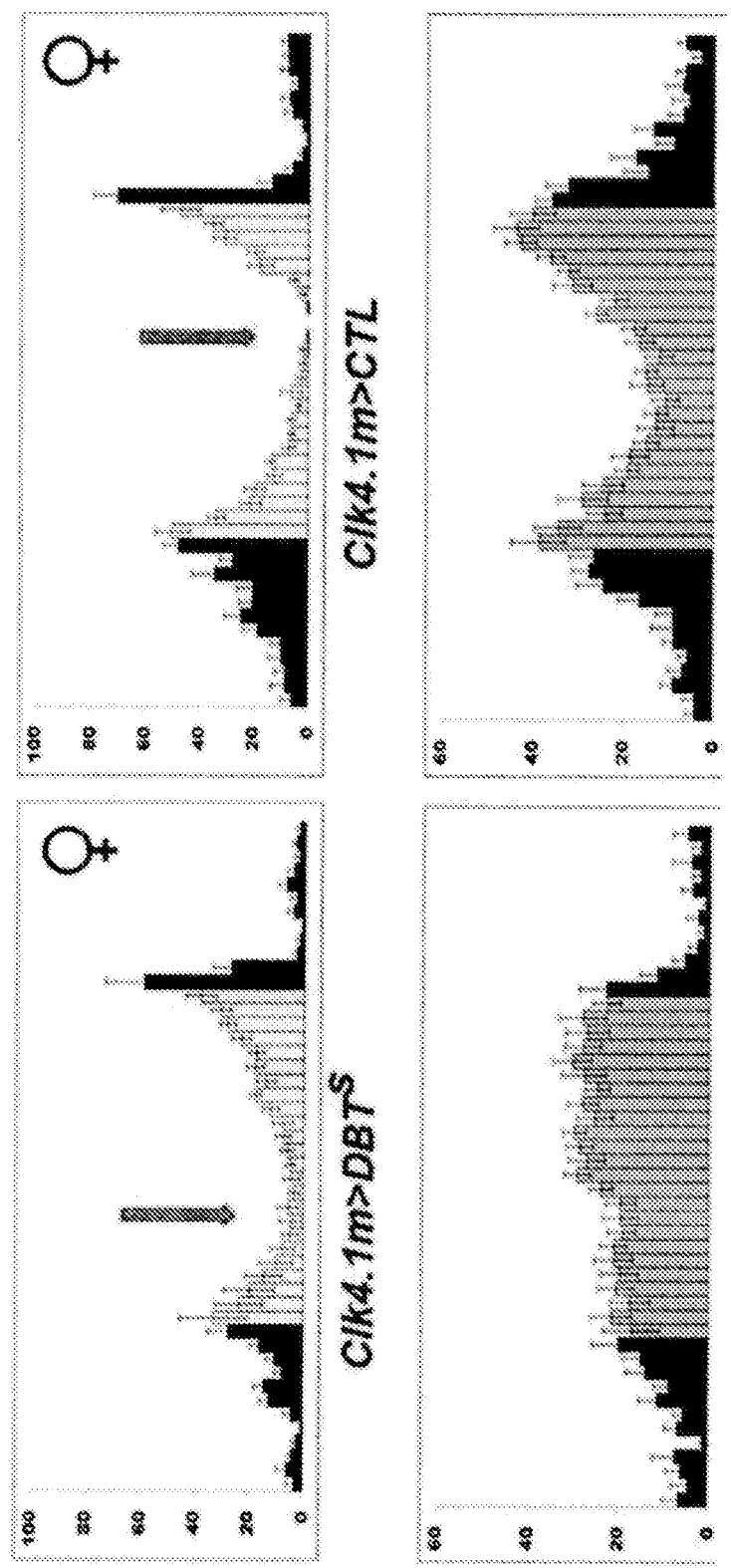
FIG. 11 are graphs showing that accelerating the clock only in the DN1s can change the timing of siesta.

The timing of the circadian clock within the DN1s and its relationship to other clock neurons is considered to be important for siesta. This is because selective overexpression of the important circadian kinase DBTS only in the DN1s (Clk4.1m>UAS-DBTS) caused an earlier siesta in LD (FIG. 11, upper panel). This indicates that events timed by the clock within the DN1s determine the timing of the siesta. In contrast, flies that overexpress the DBTS allele everywhere in the nervous system manifest a short circadian period in DD (about 21 hr) and an advanced E peak in LD. In addition, DN1-specific overexpression of DBTS effectively eliminated the siesta in DD: these flies manifested only one major activity peak rather than the typical bimodal DD pattern (FIG. 11, lower panel). A simple interpretation is that the DN1s functionally interact with other circadian neurons to generate the siesta, e.g., the daily 3 hr shift in timing of DN1 neuronal activity places it too far from the other circadian neurons with which it must communicate during extended incubation in DD, discussed below.

Figure 4A:
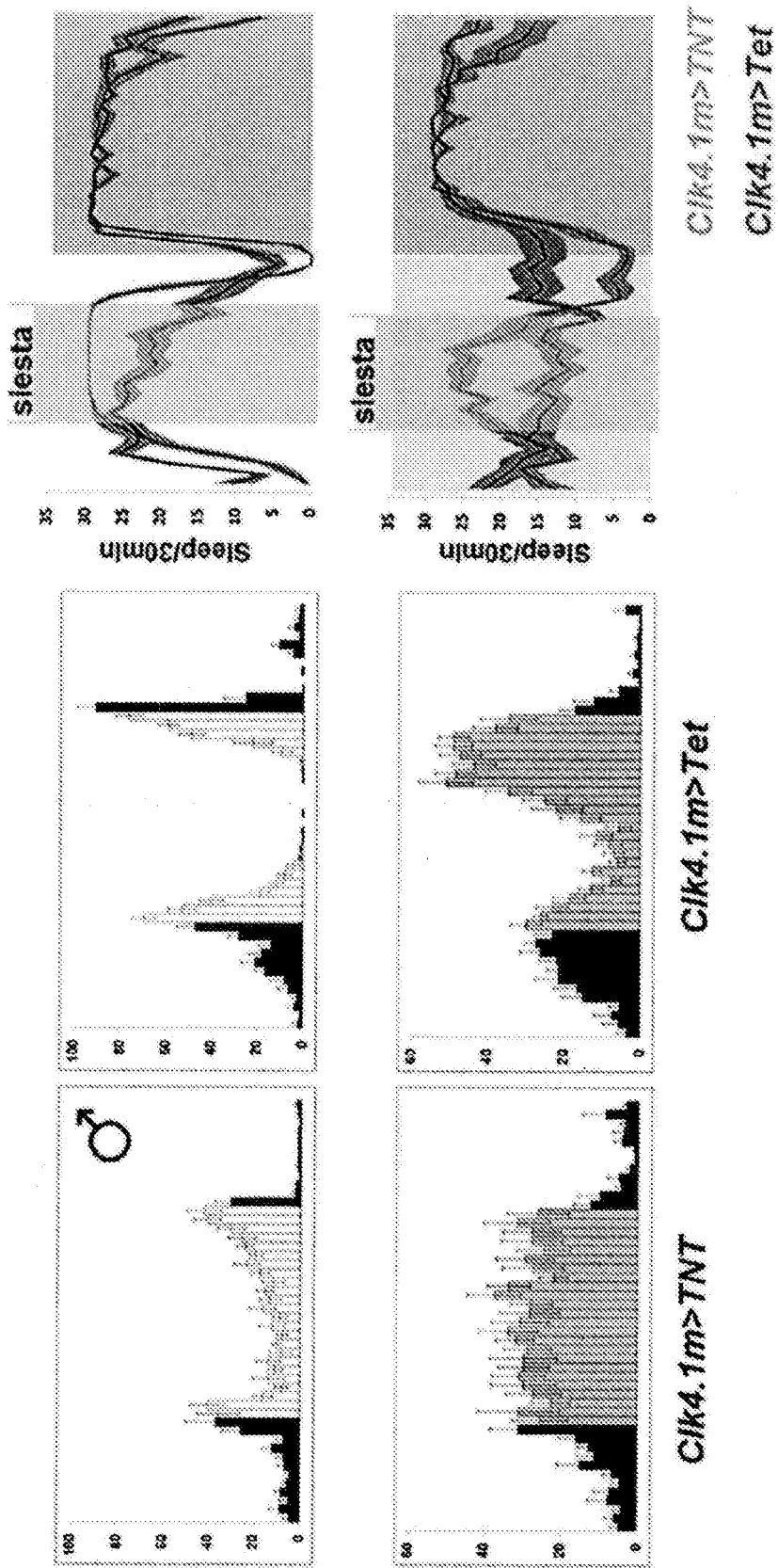
FIG. 4A shows graphs of example average activity and sleep data of the experimental and control male flies is shown in light dark ("LD") (upper panel) and constant darkness ("DD") (lower panel) conditions.
Figure 12:
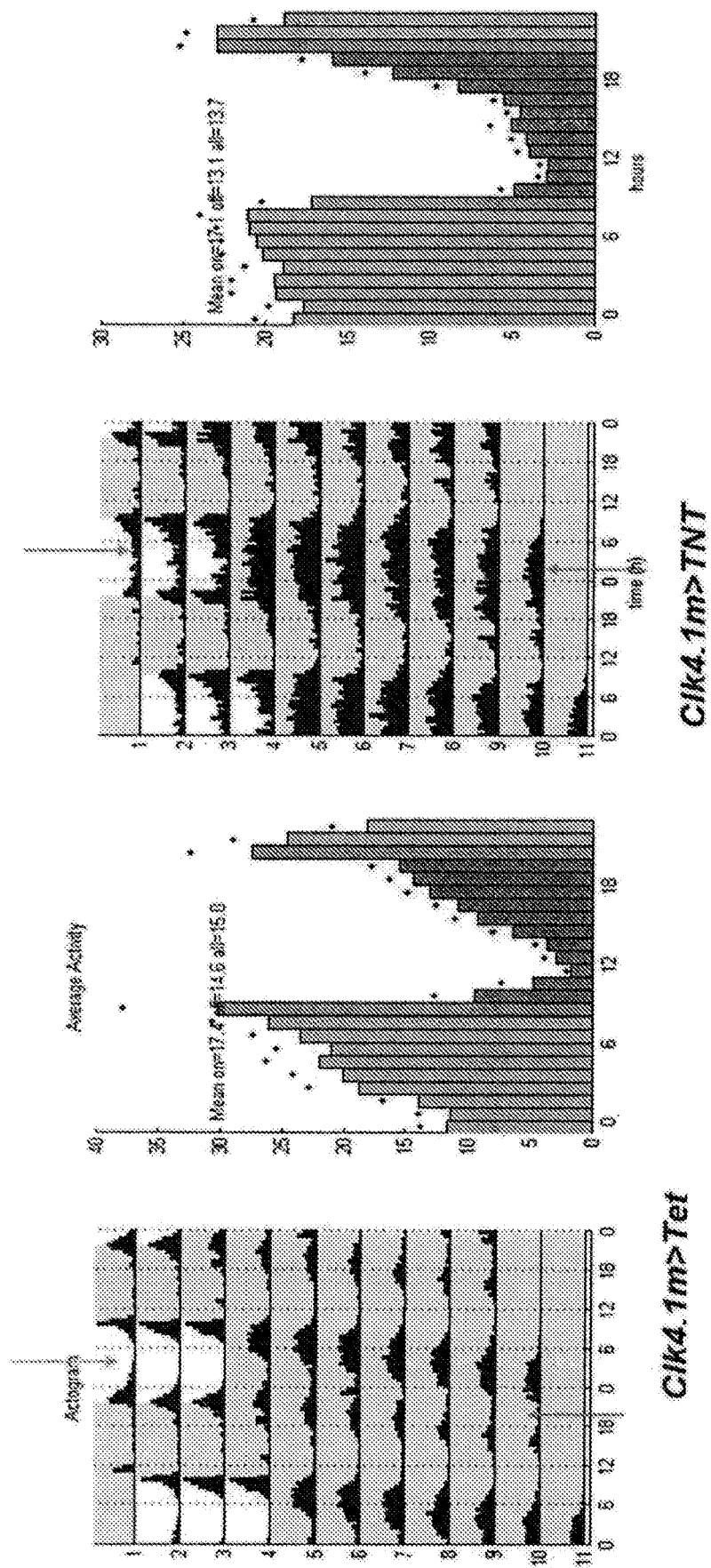
FIG. 12 are graphs showing neurotransmitter output from DN1s are not necessary for DD rhythmicity.

To further address the function of the DN1s in the siesta, the synaptic neurotransmitter blocker TNT was expressed with the same DN1 driver Clk4.1M-GAL4; the inactive toxin Tet served as a control and was assayed in parallel with same driver. In male flies, DN1 silencing with TNT caused a decrease in the morning anticipation peak under DD as well as LD conditions and a decrease in the lights-on induced startle response (FIG. 1A). These effects are expected and consistent with previous reports showing that DN1s contribute to these two morning-specific behaviors. Notably however, the male mid-day siesta in LD is strikingly decreased after silencing DN1s (compare top left and right of FIG. 1A) and is essentially absent in DD (bottom left, FIG. 4A). These activity profiles of the DN1-blocked flies in DD indicate that they are still rhythmic in constant darkness. This was confirmed by quantitative analysis under prolonged DD conditions (FIG. 12), indicating that free-running rhythmicity does not require neurotransmitter output from DN1s. Also as suggested by the activity profiles (FIG. 4A), sleep during the middle of the day (ZT3-ZT9 or CT3-CT9) is reduced by DN1 silencing, with a more prominent effect in DD than in LD (FIG. 4A).

These results indicated that that some light (daytime) suppression of activity in the mid-day occurs independent of normal DN1 output but that the circadian clock-generated siesta requires DN1s. The data moreover indicated that the striking evening peak observed in males was linked to DN1-mediated siesta, further suggesting that the evening peak is a circadian circuit feature rather than due to the activity of a single group of circadian neurons.

Figure 4B:
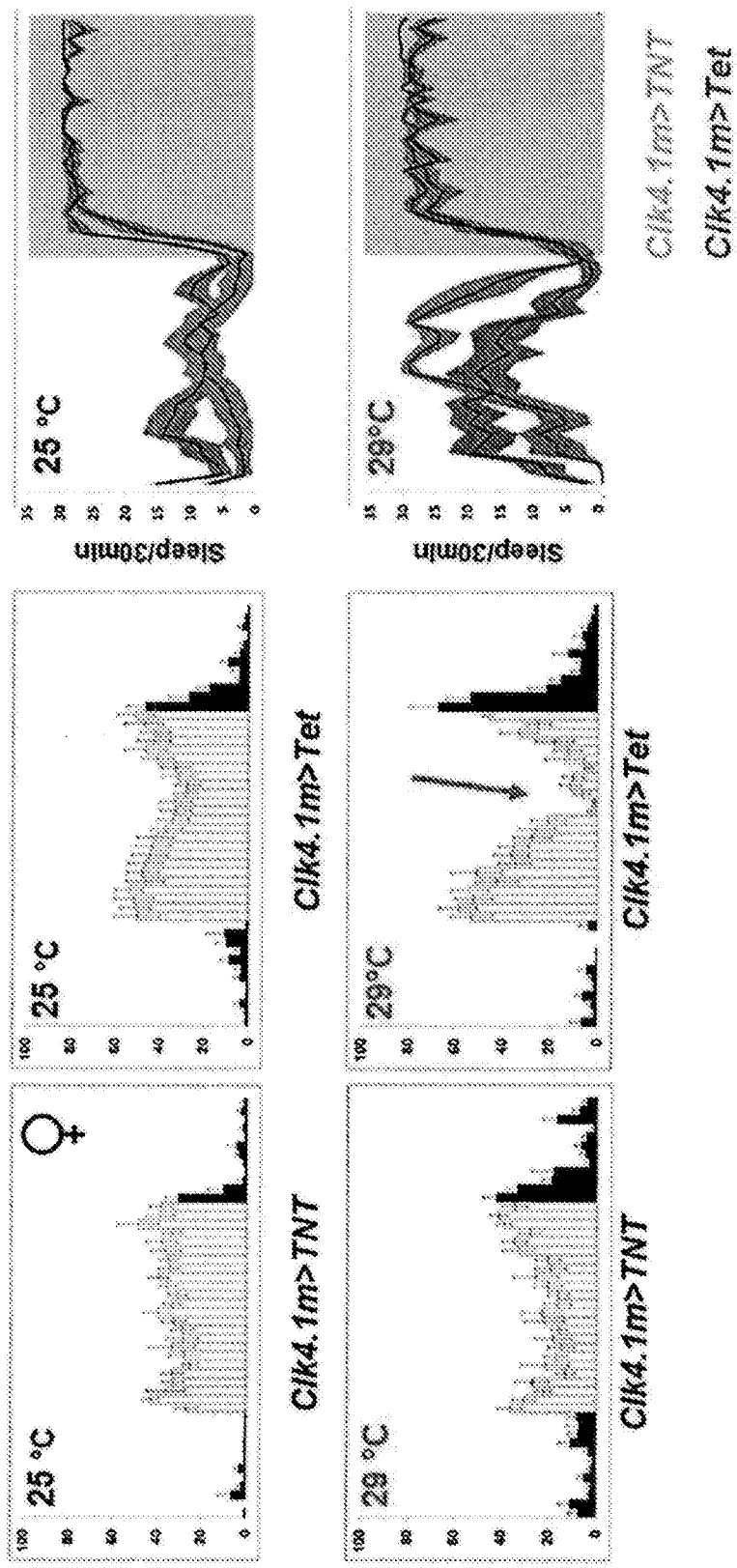
FIG. 4B shows graphs of example activity and sleep data of the experimental and control female flies in LD at normal temperature (upper panel) and higher temperature (lower panel).

Higher temperatures have been shown to increase the siesta and delay the evening peak in flies; these adjustments may be adaptations to seasonal changes, i.e., more summer-like conditions. This was particularly notable in females, which have a dramatically different daily locomotor activity and sleep pattern compared to males. Females manifested reduced morning activity, a much less robust siesta and a less pronounced evening peak because of the more uniform daytime activity (FIG. 10). As such, a warmer temperature (29° C.) caused a dramatically enhanced midday siesta in control females (FIG. 4B lower panel right; Clk4.1m>Tet). This temperature effect was blocked by TNT expression (FIG. 4B. lower left, Clk4.1m>TNT). Blocking DN1 output had a much less pronounced effect on females at normal temperatures (25° C.) as one might anticipate from the much more modest female siesta at this temperature (FIG. 4B, upper left). An enhanced siesta and a delayed evening peak were also apparent in males (FIG. 13), both of which were substantially reduced when the DN1s are silenced.

Figure 14:
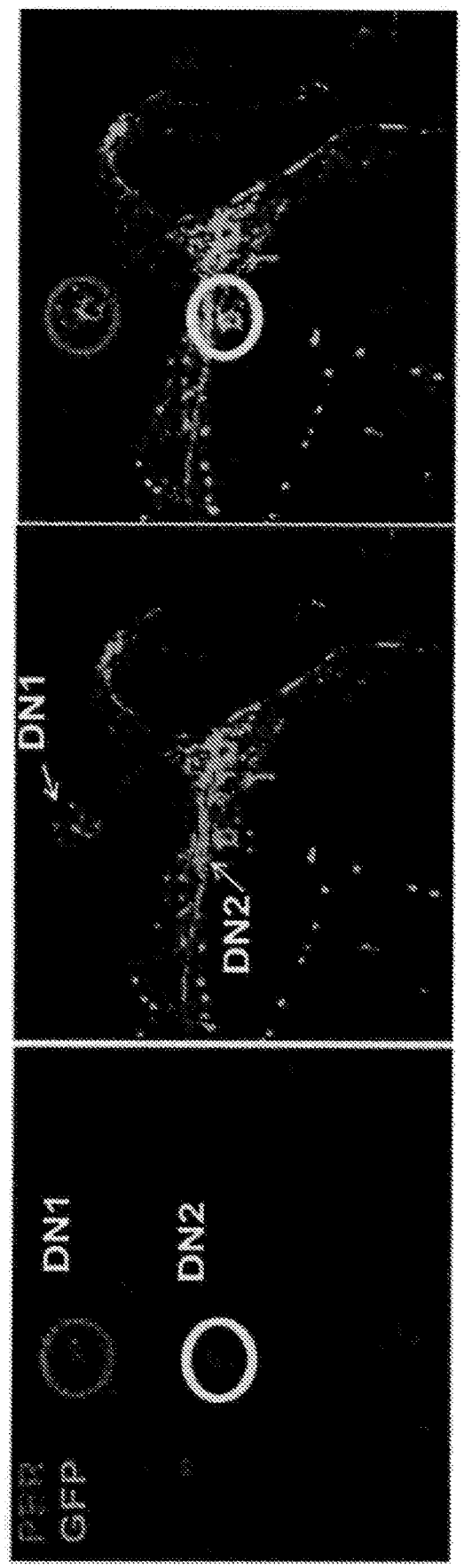
FIG. 14 are images showing the expression pattern of Pdfr (R18h11)-Gal4.

To avoid a possible complications from TNT expression during development, DN1s in females were temporally silenced only during the adult stage. To this end, the potassium channel UAS-Kir was expressed, as well as Tub-GAL80ts, with two different drivers (R51H05-GAL4 and R18H11-GAL4), which label subsets of the DN1s (FIG. 14). These were identified from screening the GAL4 collection recently generated at Janelia Farm Research Campus. Tub-GAL80ts blocked GAL4 activity at low temperature (21° C.) but lost its inhibitory activity at higher temperatures (30° C.). With both drivers, the flies had a quite normal female activity pattern at 21° C. At 30° C. however, control female flies showed a dramatically enhanced siesta as well as a reduced and delayed evening activity peak. (Compare the top left and top right of FIG. 4C.) However, females with silenced DN1s still exhibited a normal E peak even at 30° C. (FIG. 4C, bottom right and middle right), confirming that warmer temperatures act through DN1s to inhibit locomotor activity in the mid-day and evening.

To address this issue in more detail, a real-time assay of neuronal activity was developed in live flies. Newly generated calcium-dependent transcription activator CaLexA was employed to drive the expression of luciferase ("LUC") in discrete neurons and assayed flies in a standard top counter machine. LUC activity is expected to reflect calcium levels and therefore neuronal excitability. Optogenetics were used to test this approach, by co-expressing the red-shifted channelrhodopsin CsChrimson and CaLexA-LUC in these same DN1 neurons and exposing the flies to a 10 min 627 nm light pulse.

Figure 5B:
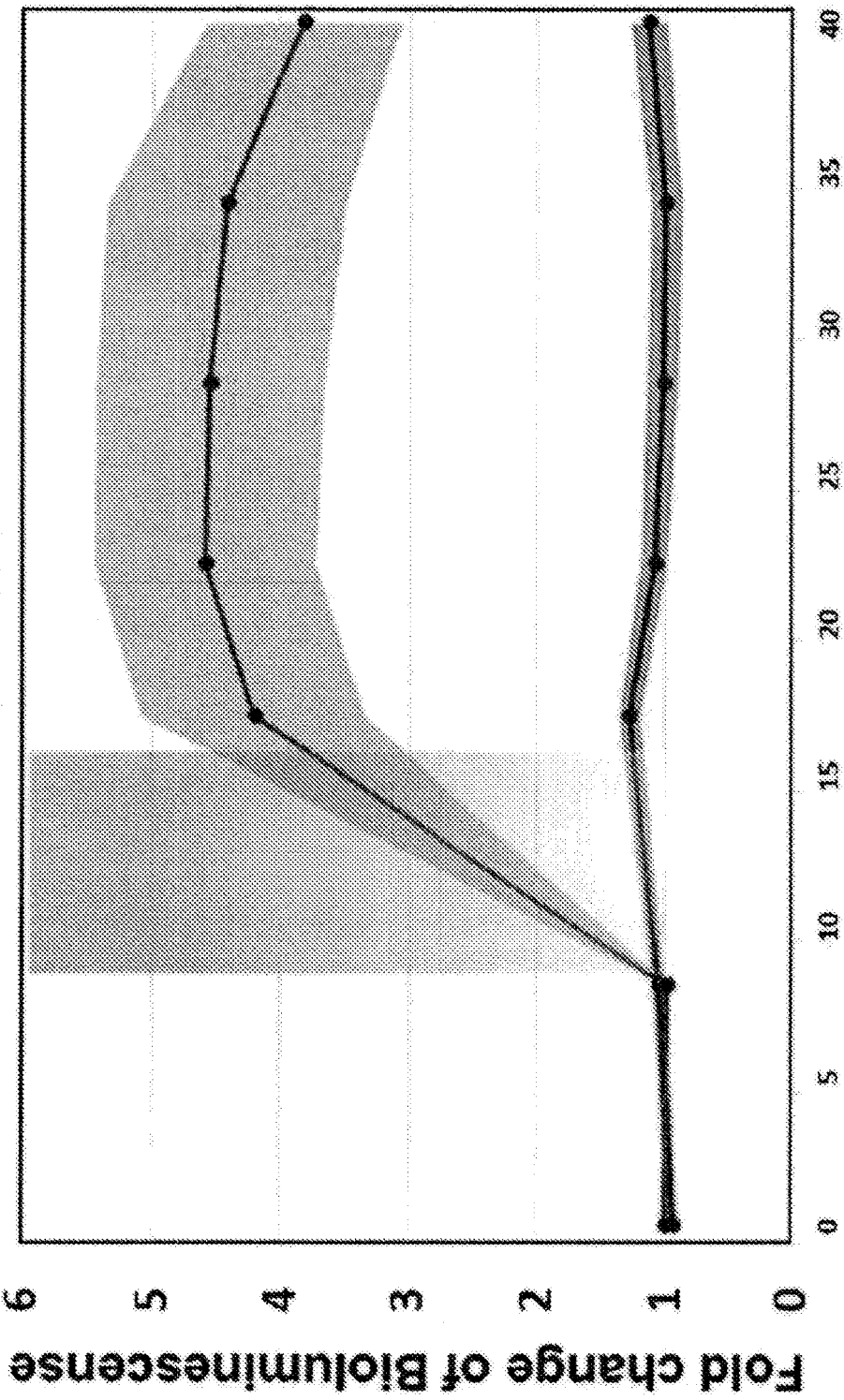
FIG. 5B shows a graph indicating example changes in neuronal activity reflected in bioluminescence data as a result of applied optogenetic stimulation, in accordance with aspects of the present disclosure.
Figure 5C:
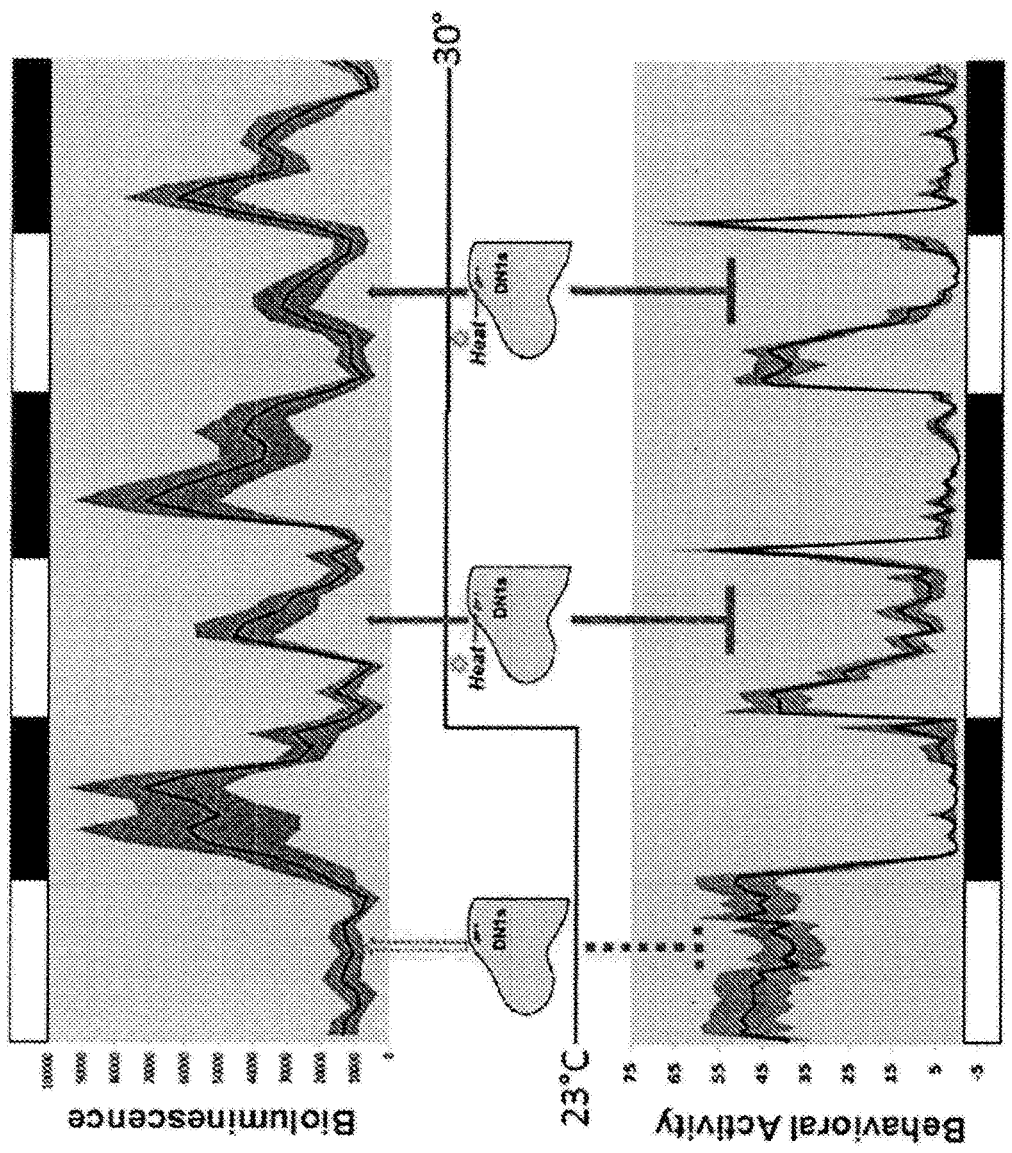
FIG. 5C shows graphs indicating correlations between behavioral and neuronal activity in female flies.

Assaying the flies in a standard Topcount plate reader indicated that the light pulse caused a dramatic increase in LUC activity (FIG. 5B). The response of CaLexA-LUC expression was then assayed in female DN1s as a function of temperature. There was a significant increase in female DN1 neuronal activity in the middle of the day at 30° C. compared to 23° C. (FIG. 5C top), coinciding with the prominent DN1-dependent temperature effect on the female siesta (FIG. 5C bottom). This indicated that temperature enhances DN1 firing, promoting the siesta. As DN1s have been reported to, express the heat-sensitive dTrpA1 cation channel, they may be intrinsically temperature-sensitive.

Figure 5D:
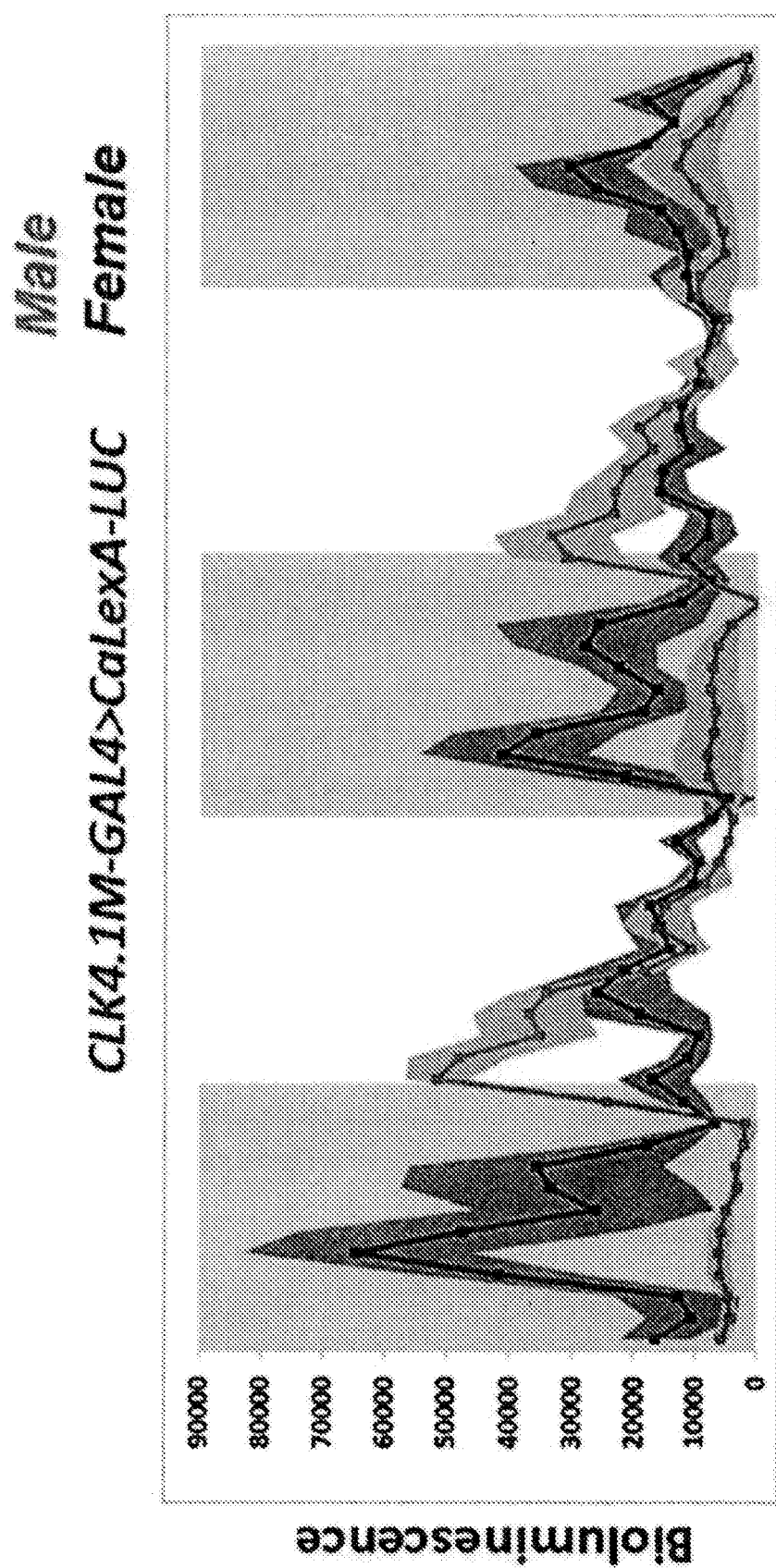
FIG. 5D shows a graph indicating differences in neuronal activity between male and female flies as reflected in bioluminescence data.

There was also a dramatic sex-specific difference in putative DN1 activity (FIG. 5D). Male DN1 neuronal CaLexA-LUC activity increased before light on, peaked during the morning and then declined to a trough in the evening. This much higher male DN1 activity during the morning and the middle of the day likely contributed to the robust morning anticipation and siesta of males. If blocking DN1 output suppressed the siesta and increased evening activity, DN1 activation would have promoted the siesta and perhaps even inhibit the subsequent evening anticipation peak. To this end, the red-shifted channelrhodopsin CsChrimson was overexpressed in DN1s, as shown above, and combined the optogenetic stimulation with behavioral monitoring in 96 well plates. The flat surface and compact wells of the plate allowed uniform illumination of wake-behaving flies, in contrast to the difficulties associated with previous technologies.

Figure 6A:
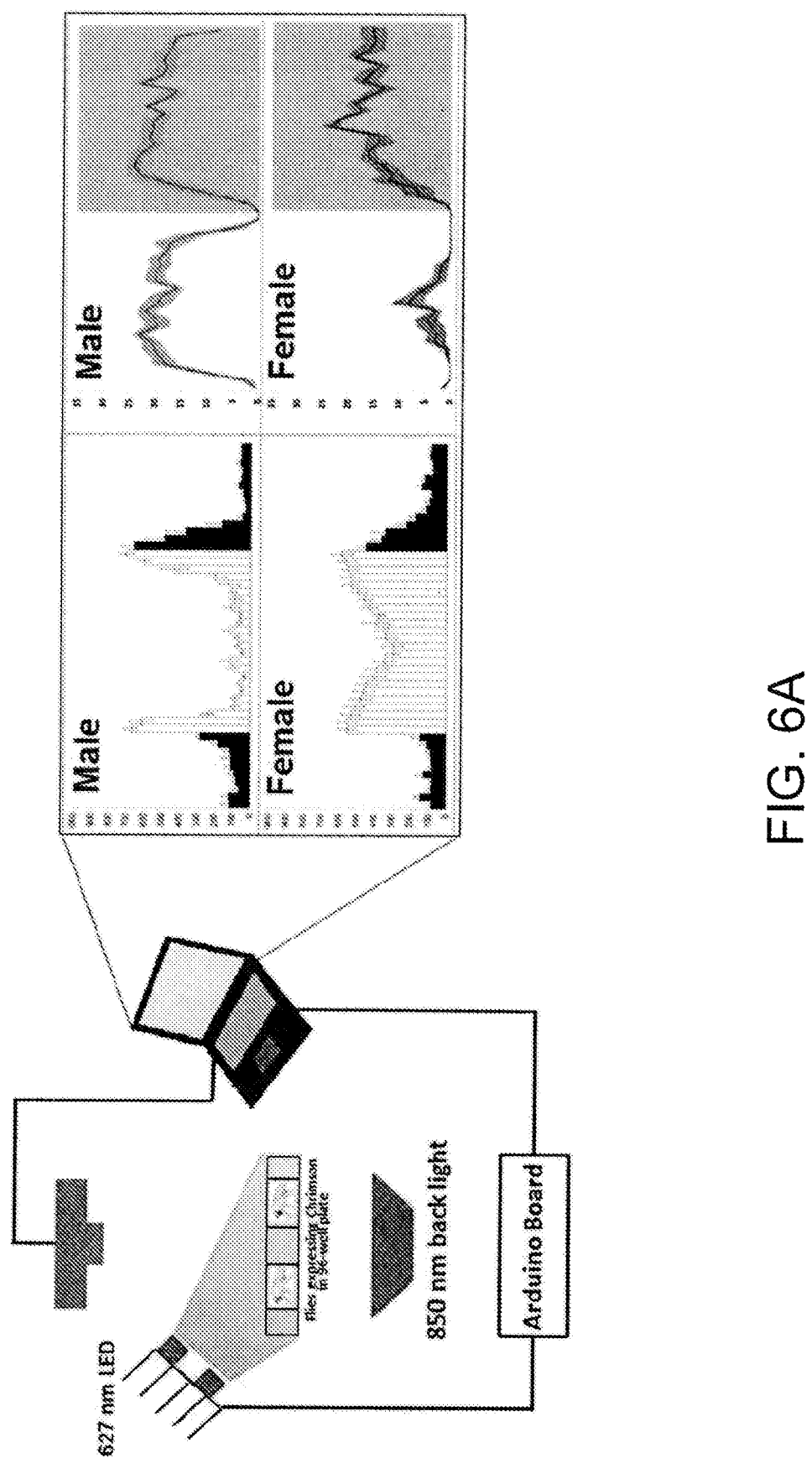
FIG. 6A is a graphical illustration showing an example measurement and stimulation configuration, in accordance with aspects of the present disclosure, and measured data characterizing male and female flies during periods of activity and sleep.
Figure 6B:
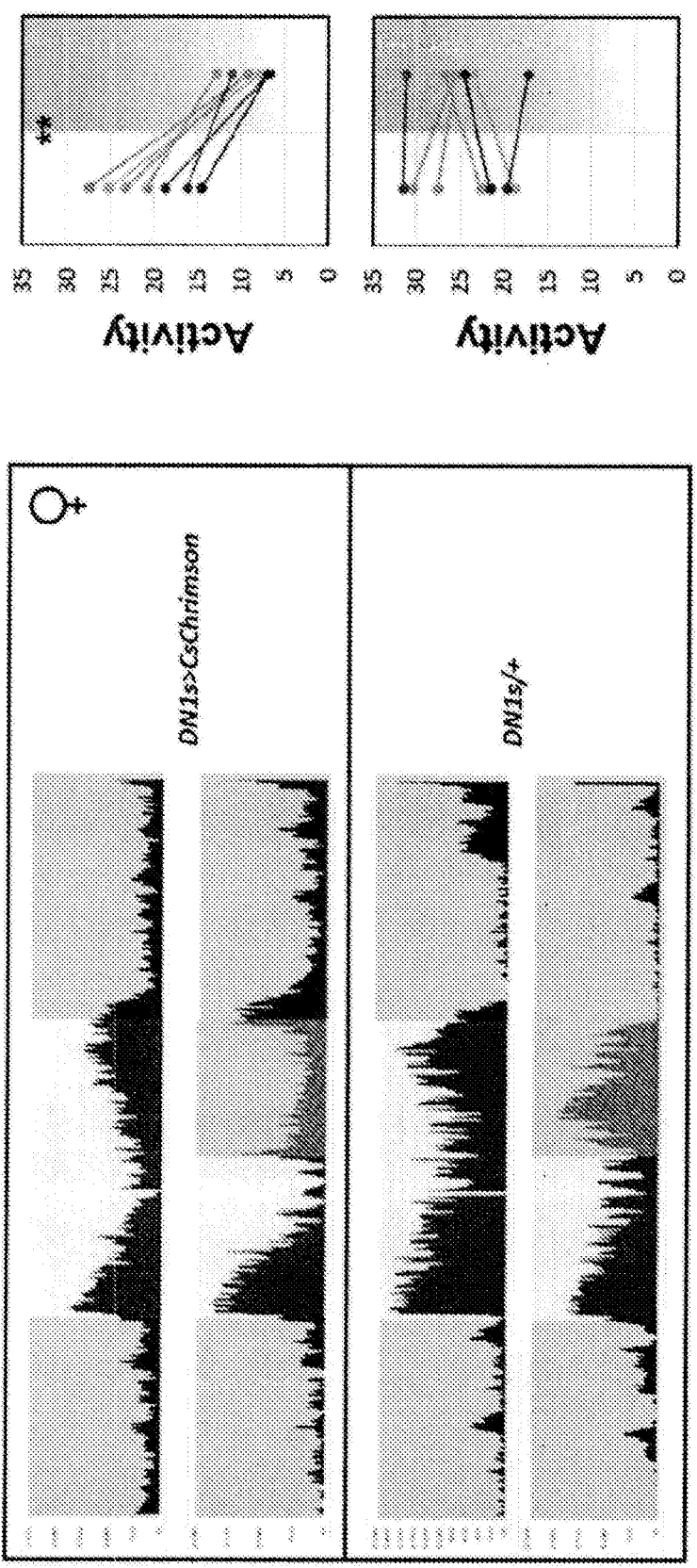
FIG. 6B shows graphs illustrating an example of changes in locomotor activity in flies due to pulsed light stimulation.
Figure 6C:
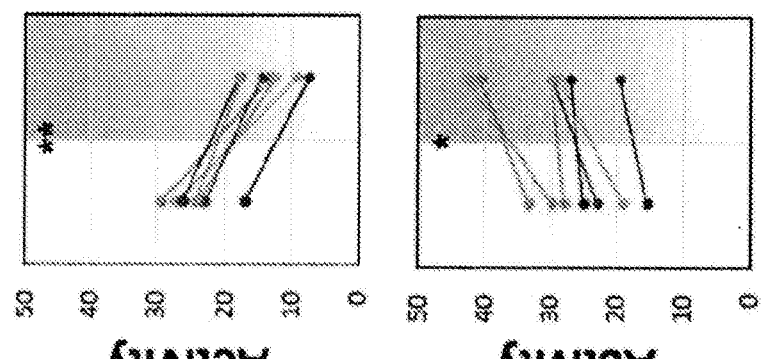
FIG. 6C shows graphs illustrating another example of changes in locomotor activity in flies due to pulsed light stimulation.
Figure 6C:
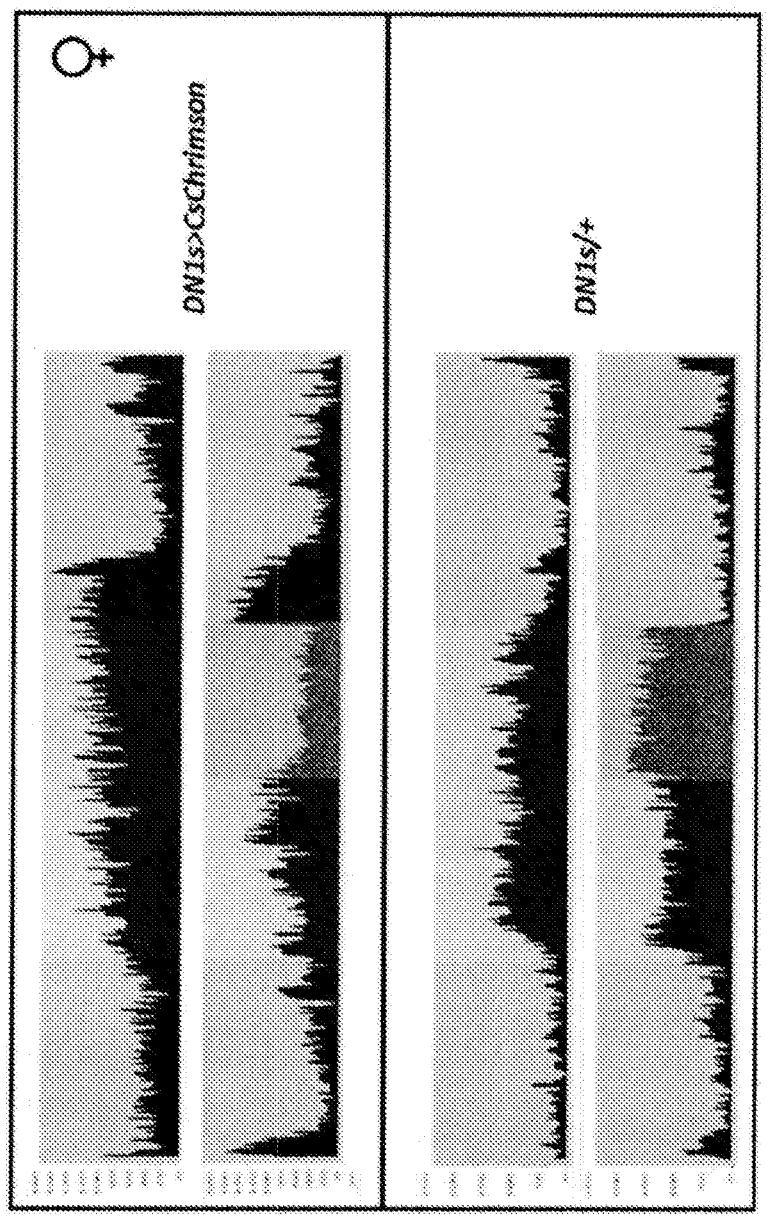
Figure 15:
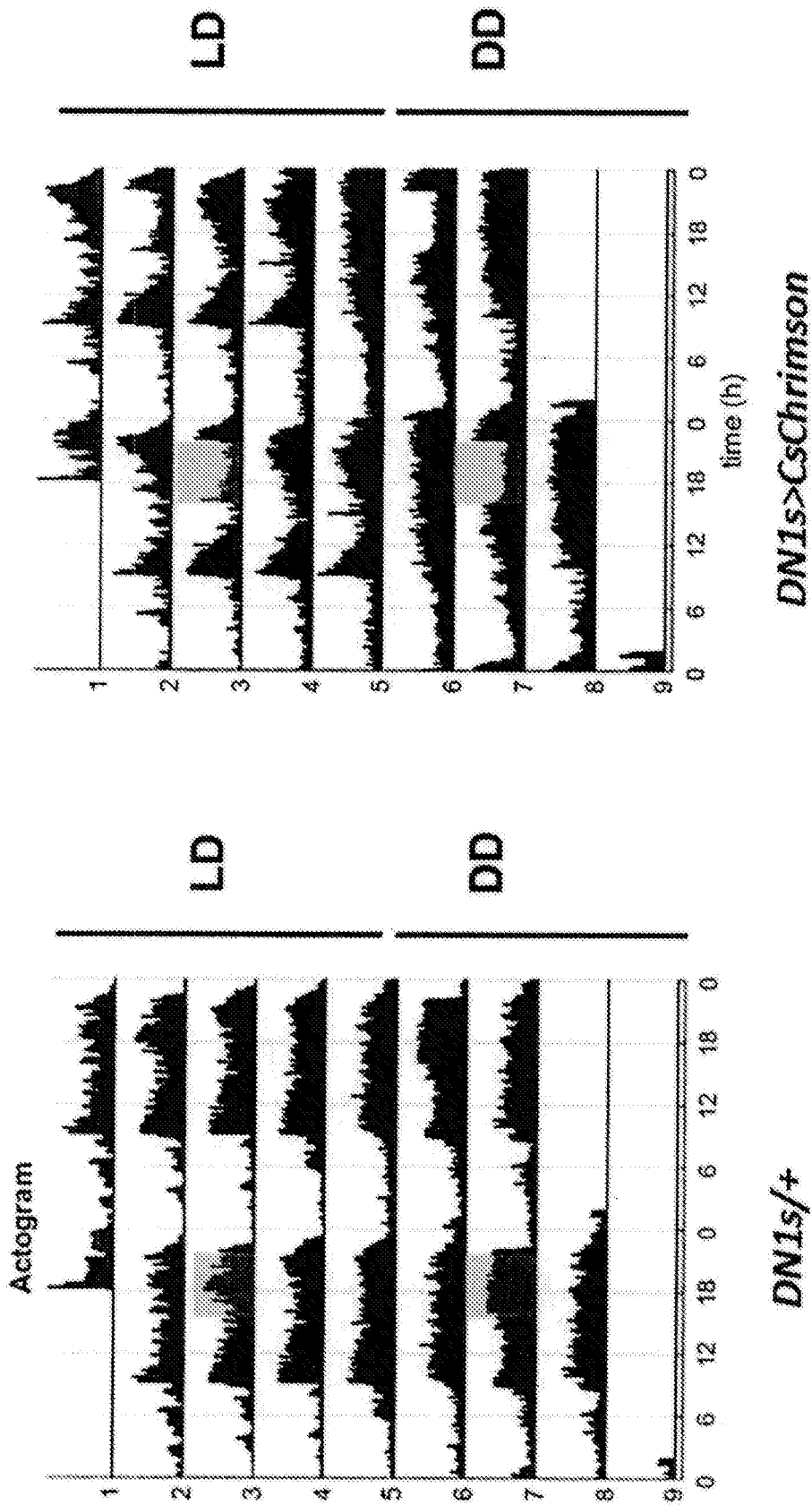
FIG. 15 are graphs showing that DN1 activation suppresses evening locomotor activity.

The assay also used a video recording system to automatically track the movement of individual flies (FIG. 6A, left). It was first verified that flies in the plate wells exhibited normal bimodal locomotor activity and sleep/wake cycles in the video recording assay as compared to the classical infrared beam-crossing Trikinetics assay, including less morning activity and siesta for females than for males (FIG. 6A, right). Then, 10 HZ 627 nm red light pulses were used to irradiate the flies expressing CsChrimson within the DN1s. The laser was turned on between ZT7-12 to examine the effect of DN1 activation on the E peak. Red light-mediated DN1 activation strongly and rapidly switched fly behavior: the flies decreased their locomotor activity and increased their sleep. In contrast, flies without CsChrimson expression were mildly stimulated by the red light illumination and behaved much more similar to the preceding baseline days, i.e., they both increased their locomotor activity and showed the expected evening anticipation peak between ZT7-12 in LD (FIG. 6B) and CT7-12 in DD (FIG. 6C and FIG. 15). Interestingly, DN1s played an opposite role during the morning, consistent with previous studies. This was because the DN1-CsChrimson flies maintained high locomotor activity when illuminated with the LED from ZT0-ZT4 (FIG. 6D).

Figure 6D:
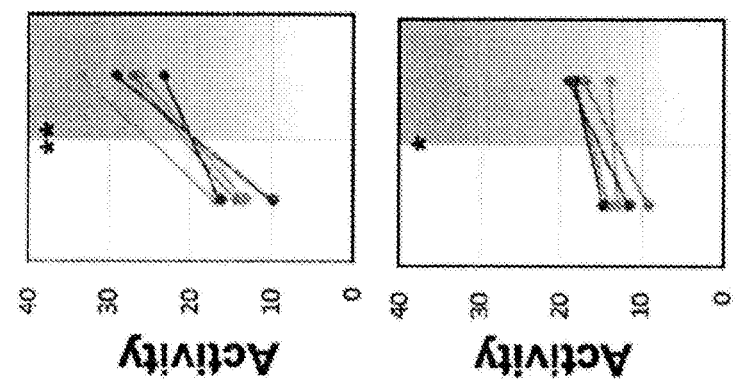
FIG. 6D shows graphs illustrating yet another example of changes in locomotor activity in flies due to pulsed light stimulation.
Figure 6D:
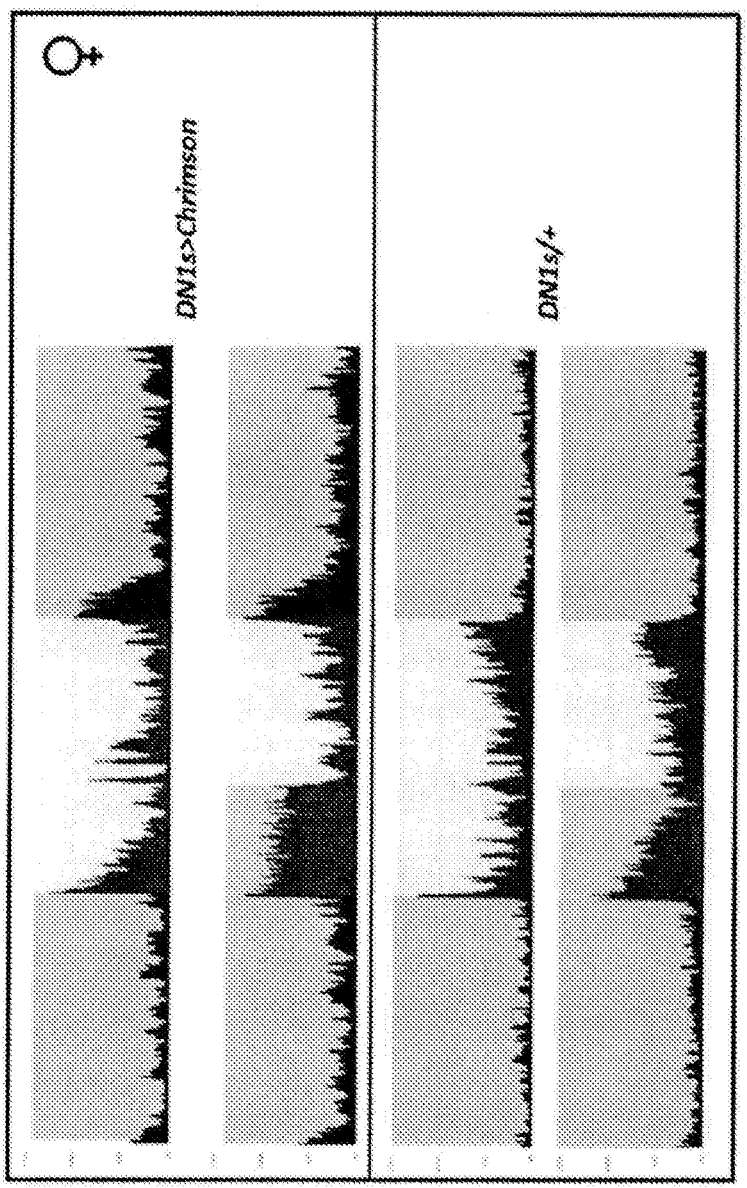
Figure 7A:
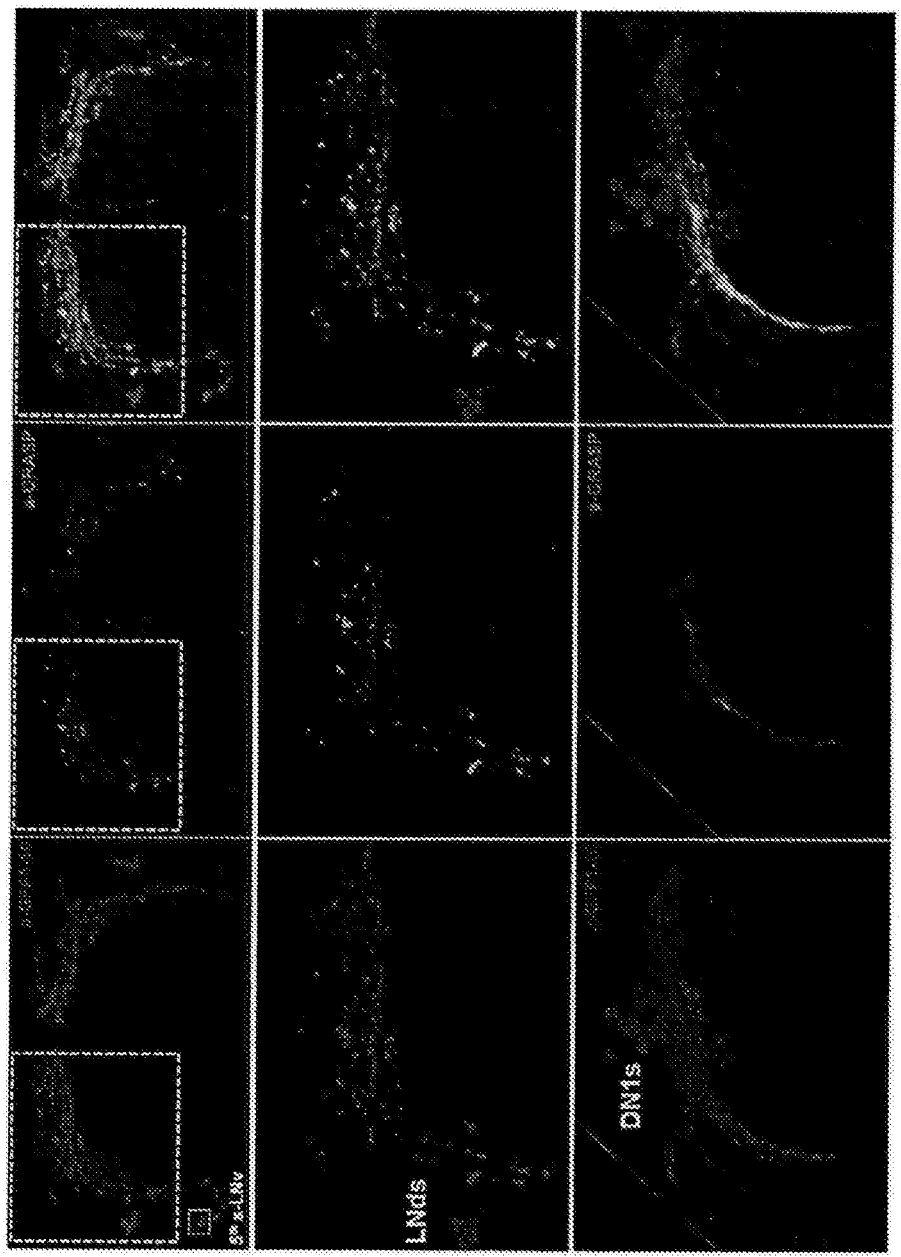
FIG. 7A is a graphical illustration showing connectivity patterns and signaling between DN1s, E cells, and PDF cells obtained from measured bioluminescence activity.
Figure 16:
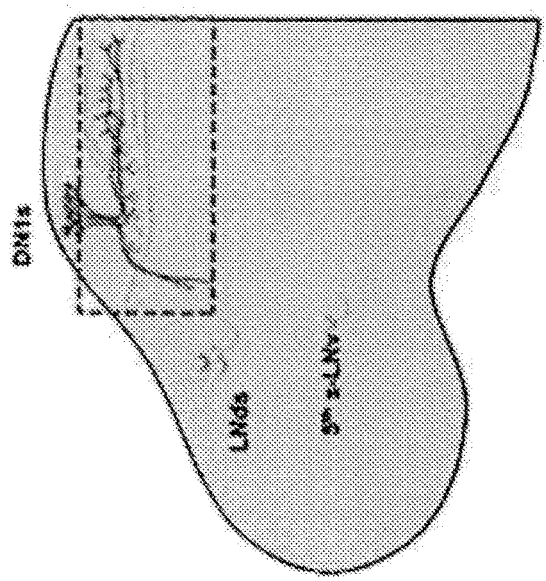
FIG. 16 is a graphical illustration showing a dendritic region of E cells overlapping with the pre-synaptic region of DN1s.
Figure 16:
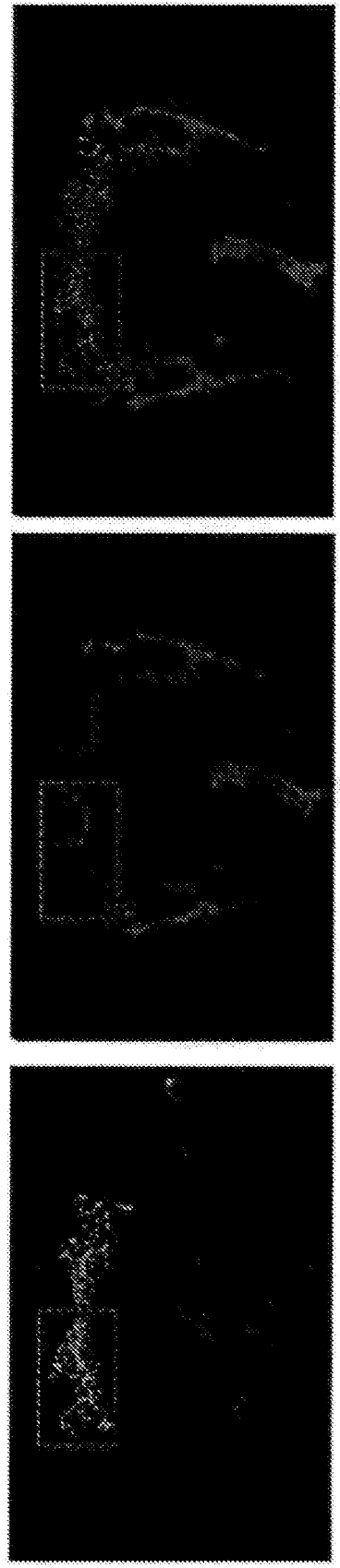

Despite comparable illumination during this 4 hr window, control flies showed a normal reduction in locomotor activity after the standard startle response to lights on stimulation at ZT0 (FIG. 6D). The data taken together demonstrate that there was an additional function of DN1 clock neurons, i.e., control of the siesta and the timing of the evening peak. Given the effects of UAS-DBTS expression in DN1s on the siesta (FIG. 11), it was considered that other circadian neurons, interacting with the DN1s might include the 5 circadian E cells, which can be targeted by DvPdf-GAL4. Moreover, the dendritic region of these E cells and the pre-synaptic region of DN1s are typically in the same area of the brain, suggesting that the interaction might be direct (FIG. 16 and FIG. 7A, cartoon on top left).

Indeed, GRASP-labeling (GFP reconstitution across synaptic partners) verified that DN1s labeled with PDFR (R18H11)-LexA and E cells labeled with Dvpdf-GAL4; Pdf-GAL80 are in close proximity. This contact occurred within the E cell dendritic region (FIG. 7A upper and middle panels; the middle panel corresponds to a magnified view of the brain region containing E cell dendrites depicted in the box on the left). The same GRASP strategy showed that DN1s also contacted the dorsal axon region of PDF cells as previously described (FIG. 7A lower panel). These anatomical data indicate that DN1s make two sets of circadian contacts, namely with PDF neurons to help promote M activity, and with E cells, to promote the siesta and modulate the E peak. Given the DN1-PDF cell contact, it is also possible that the functional interaction between DN1s and E cells is indirect, for example via the direct connection with PDF neurons. These would then contact E cells via PDF-PDFR contacts.

Figure 7A:
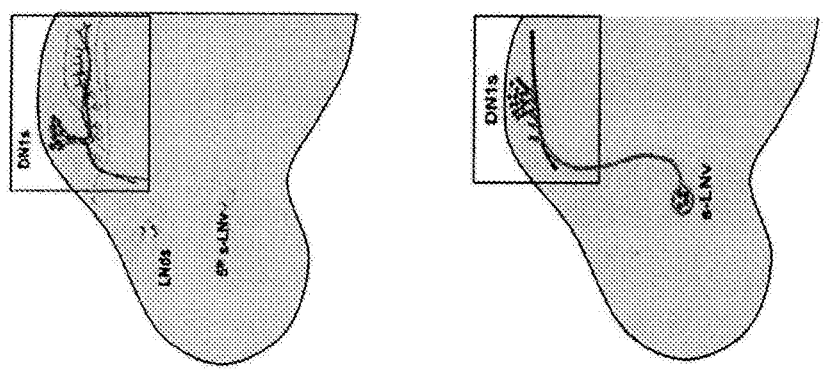
Figure 7B:
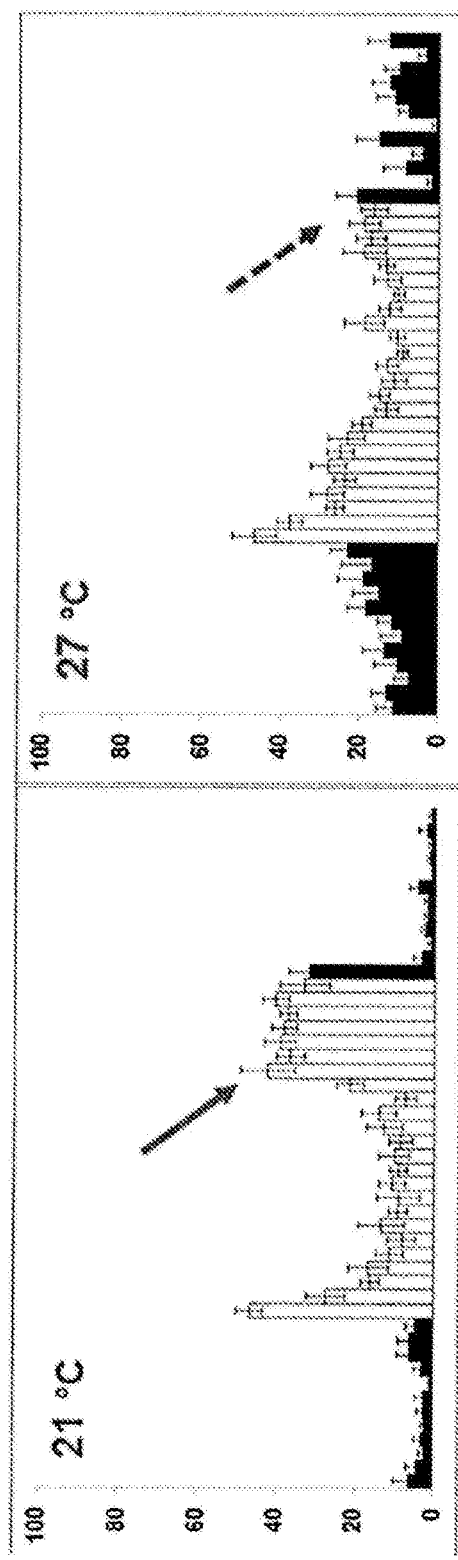
FIG. 7B shows graphs comparing activity at different temperatures, showing that DN1 activation inhibits the E peak in a mutant background.

To test this possibility, DN1s was activated in pdfr mutant flies. These flies normally manifest a robust and advanced E peak. Activation of DN1s eliminates this E peak as in a wild-type control background (FIG. 7B), indicating that the DN1s do not function via PDF signaling and consistent with a direct DN1 effect on E cells. The question then becomes how the DN1-E cell interaction might function to modulate the siesta and evening peak. Immunostaining of DN1s indicated that they express glutamate, which often functions as an inhibitory neurotransmitter in the fly central nervous system. Moreover, RNA profiling of DN1s showed that they are much enriched in mRNA encoding the vesicular glutamate transporter Vglut (data not shown).

Figure 8A:
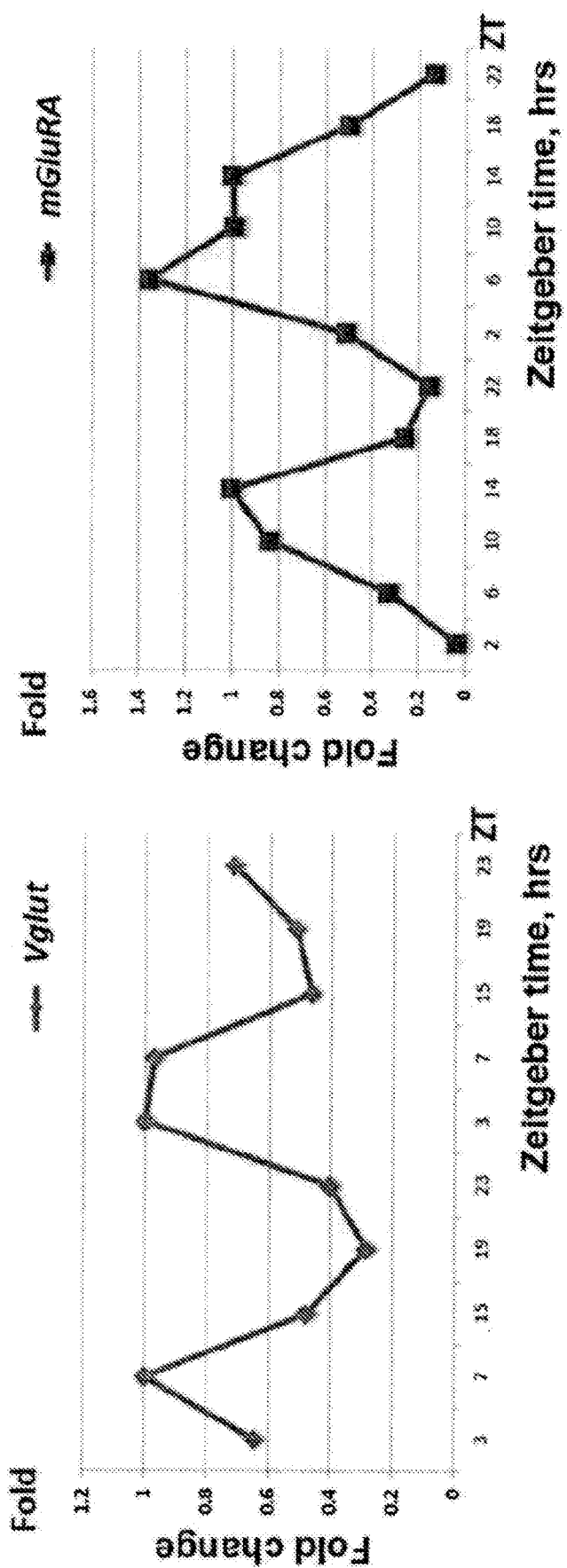
FIG. 8A shows graphs showing cycling inhibitory glutamate signals from DN1s to E cells that modulate siesta and size of the E peak.

As similar profiling of E cells indicated expression of the glutamate metabatrophic receptor mGluRA (data not shown; this the only Drosophila mGluR that can inhibit intracellular calcium in neurons), these two sets of neurons were purified at different circadian times and mRNAs were examined for circadian cycling. Both Vglut mRNA in DN1s and mGluRA mRNA in E cells strongly cycled. That is, they both reached a peak around ZT 7-14 and a trough during the night-early morning (FIG. 8A). The data are consistent with a previous study and can explain how activation of DN1s has an inhibitory effect on E cell-derived locomotor activity only in the late daytime and how other DN1 interactions predominate at other times of day, i.e., with PDF neurons in the late night-early morning (see Discussion).

Figure 8B:
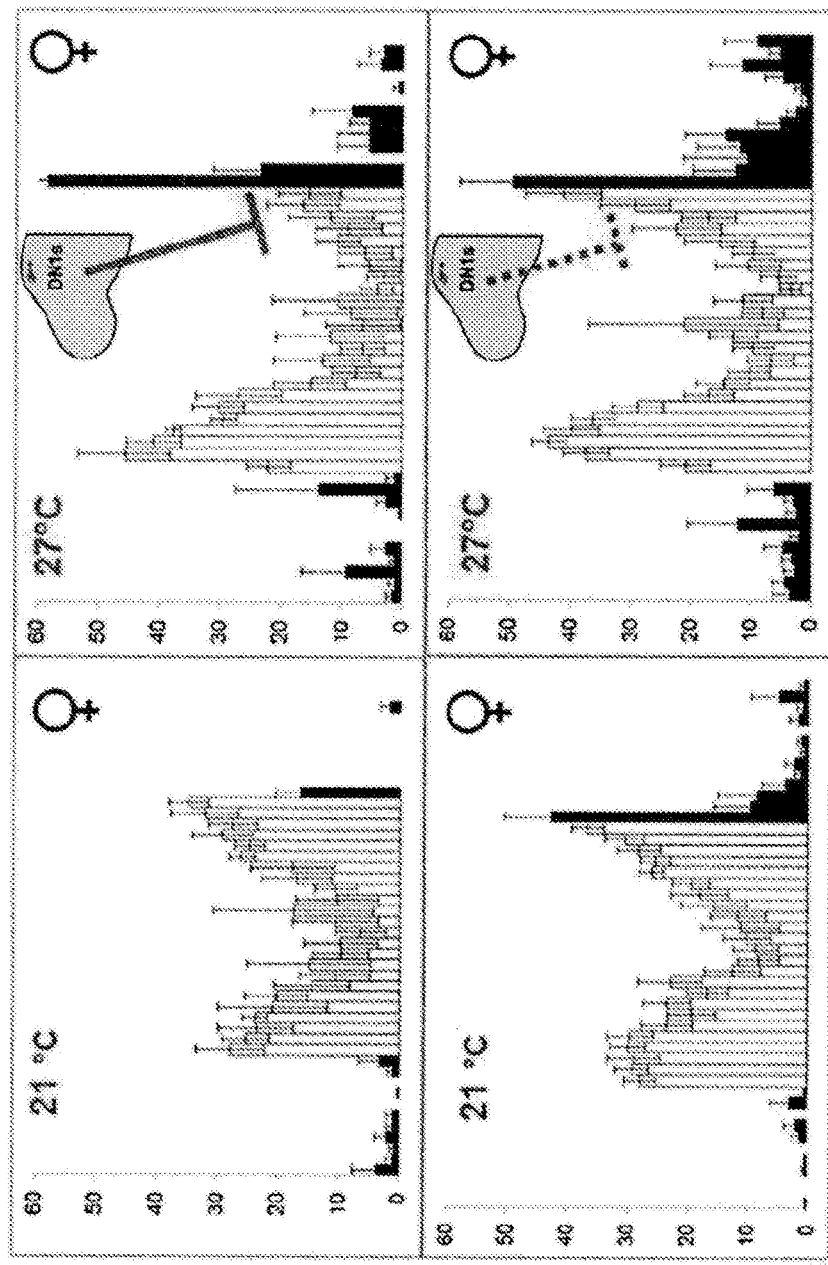
FIG. 8B shows graphs showing the activity patterns of female flies at different temperatures.
Figure 8C:
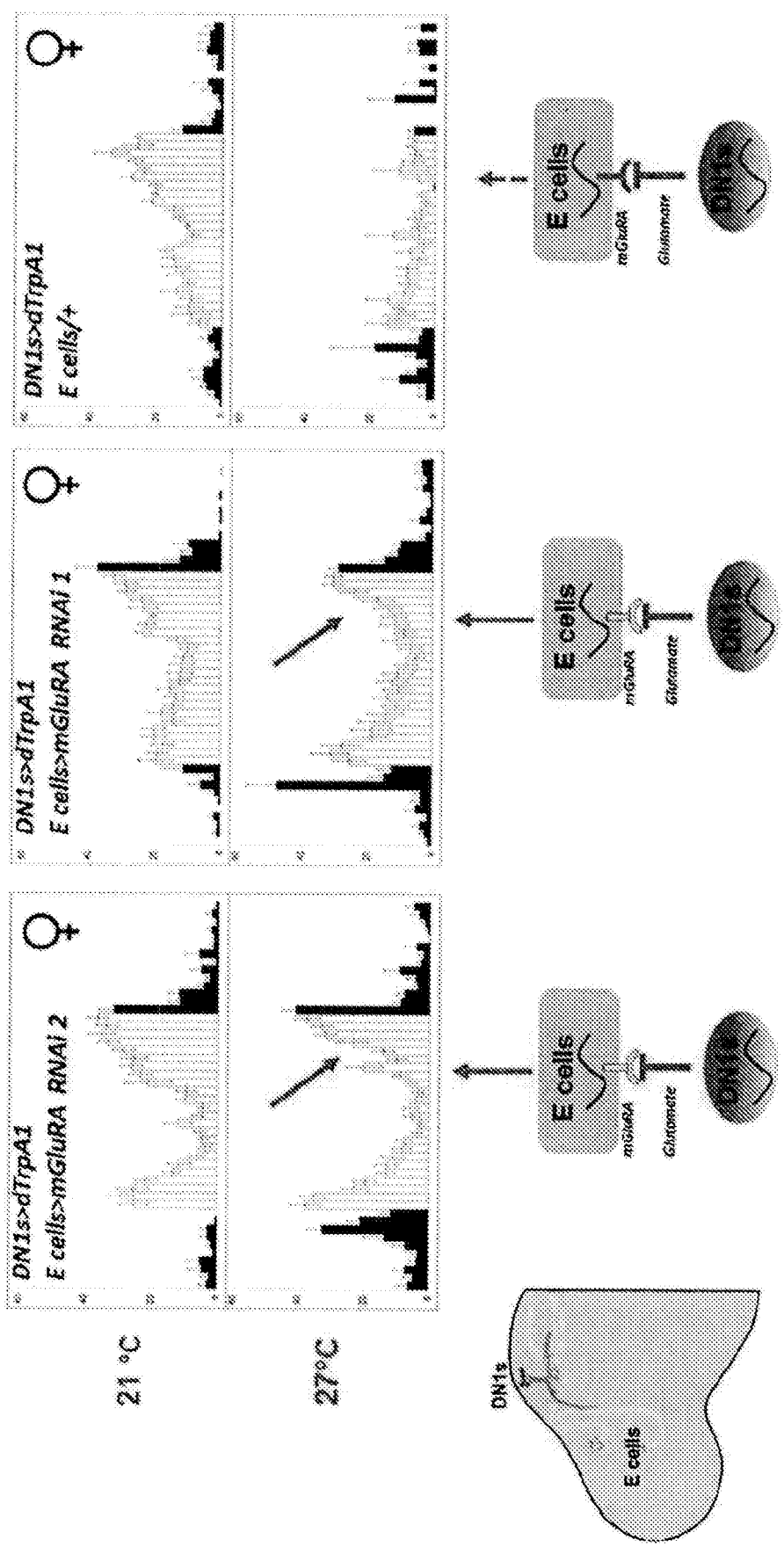
FIG. 8C is a graphical illustration comparing changes in activity patterns of female flies at different temperatures and how reducing mGluRA signaling within Ecells affects behavior.
Figure 17:
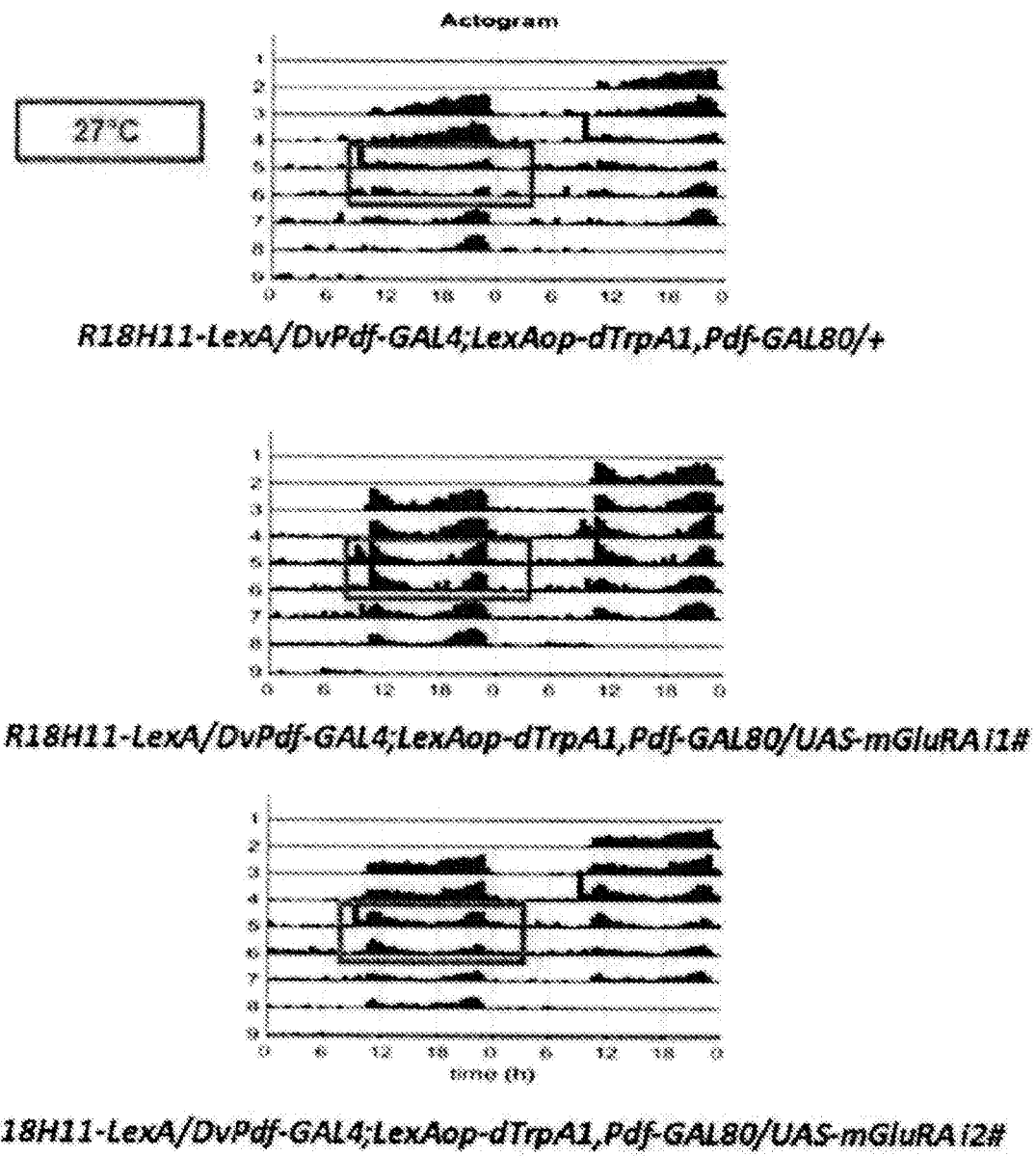
FIG. 17 are graphs showing the 7 day locomotor activity pattern of two different mGLuRA knockdown flies.

It was tested whether reduction of glutamate release from the DN1s inhibited the DN1 firing effect on the E activity peak. Indeed, flies co-expressing dTrpA1 and Vglut RNAi maintained a higher E activity peak than flies with dTrpA1 expression alone (FIG. 8B). A similar RNAi strategy to address the importance of mGluRA expression in E cells also blunted the effect of DN1 activation (FIG. 8C and FIG. 17). Although these RNAi results do not show that the mRNA cycling was significant, they do support a functional inhibitory connection between DN1s and E cells via glutamate signaling. They also add to the evidence that DN1s have a major influence on the locomotor activity pattern by promoting the siesta in a temporal, gender and temperature-dependent manner (FIG. 9).

Discussion

Figure 9A:
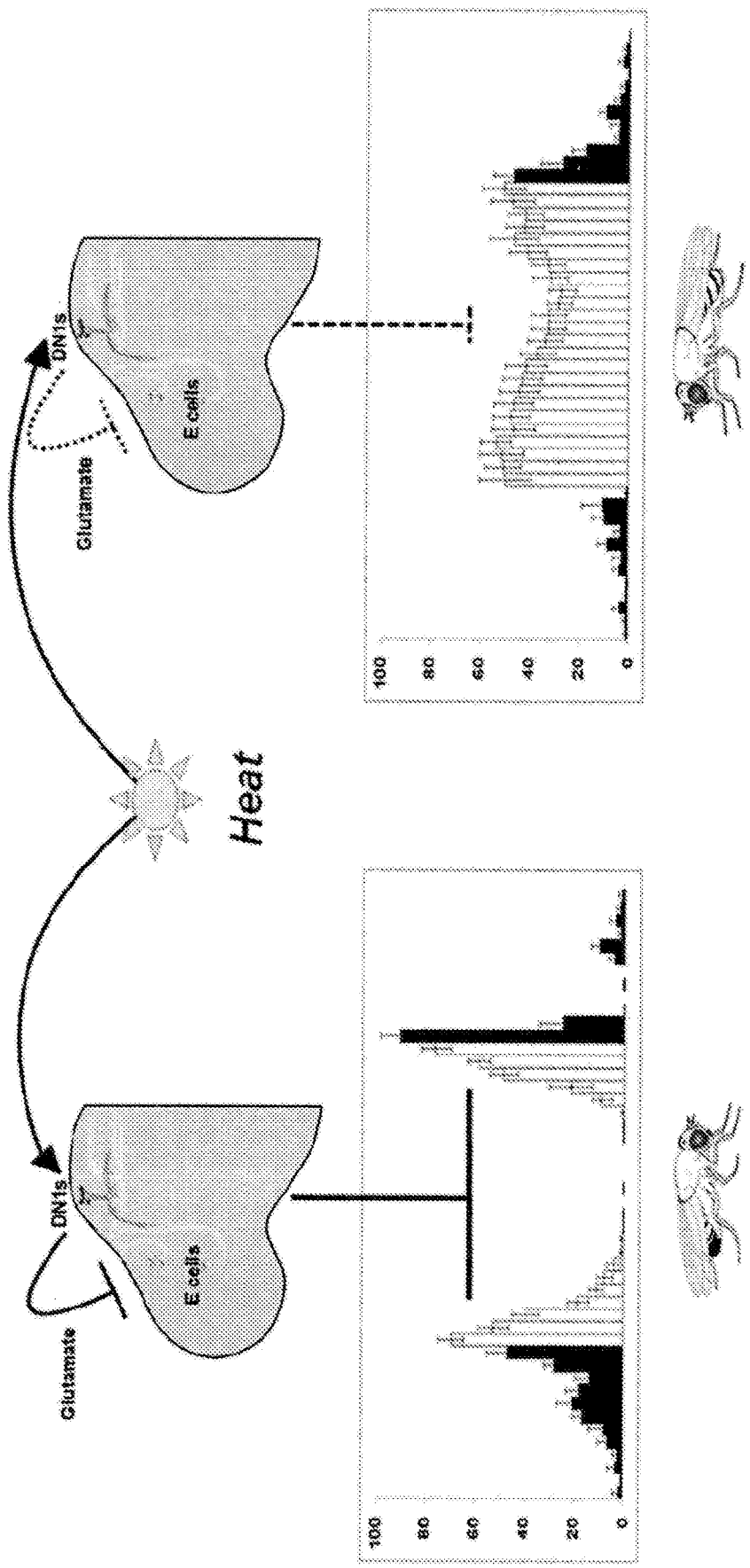
FIG. 9A is a graphical illustration showing that DN1s in male flies have a higher daily activity compared to female flies.

The classical Drosophila bimodal LD behavior pattern is observed to occur in males and was controlled by a dual M-E oscillator system in the fly brain. Although female flies have the same set of circadian cells with no described anatomical differences from males, they exhibit a very different behavioral pattern. Herein it was shown that the gender-specific siesta and E activity peak was due to the sexually dimorphic activity of DN1 s (FIG. 9A). These dorsal circadian neurons are downstream from PDF-positive M cells, and it was shown here that they also connected to E cells, which are major locomotor activity output neurons. The data indicated that the DN1s inhibit the activity of the E cells in a circadian manner to create the siesta and major features of the E peak. This modulation was demonstrated to be due at least in part to glutamate release from DN1s onto the mGluRA glutamate receptor of E cells. DN1s also integrated temperature information to modulate E cell activity.

Figure 9B:
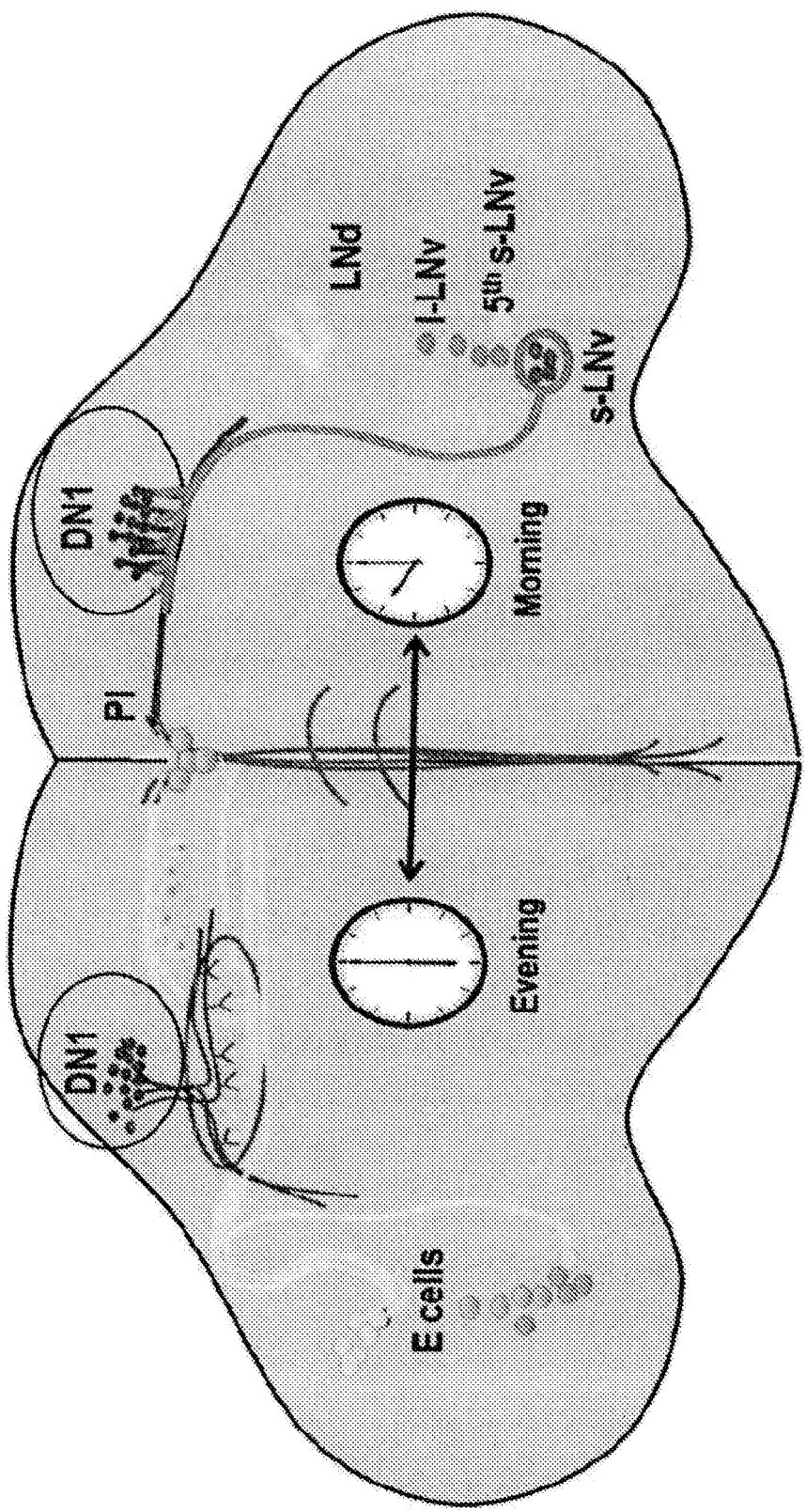
FIG. 9B is a diagram showing a model of DN1 function, its regulation and its relationship to the rest of the circadian network.
Figure 13:
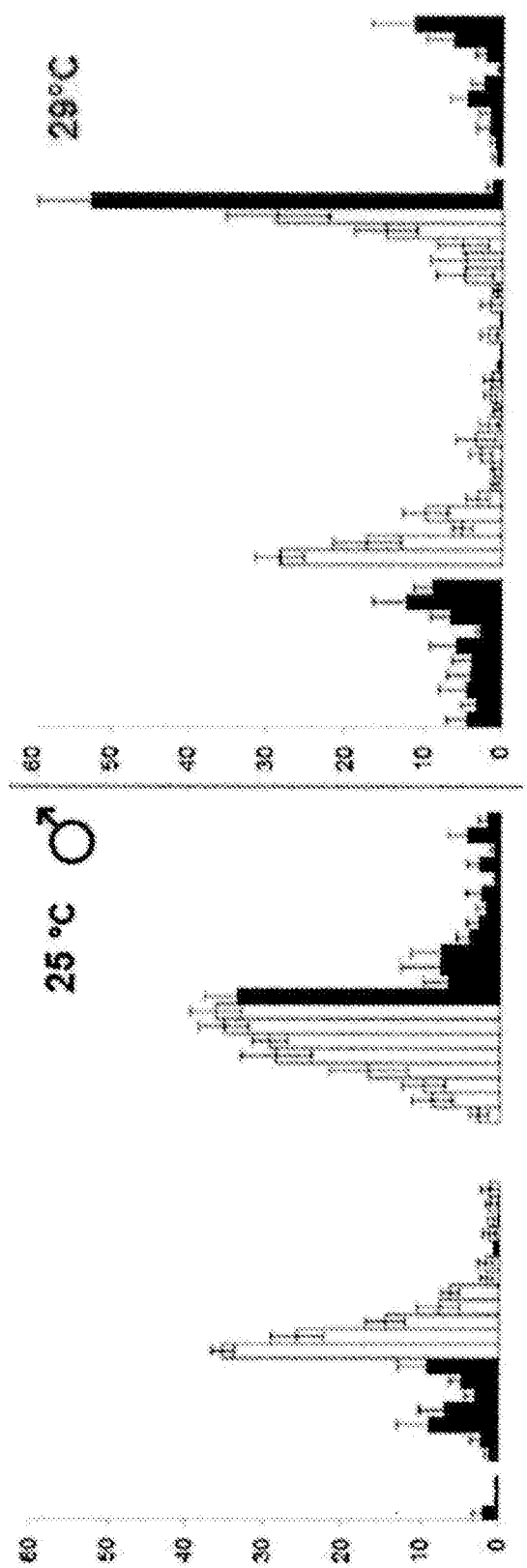
FIG. 13 are graphs showing suppressed evening peak in males at high temperatures.

One conclusion of these experiments is that the DN1s can perform multiple behavioral roles by functionally interacting with different elements of circadian circuitry at different times of day (FIG. 9B). A second conclusion is that the striking bimodal activity pattern observed in males can be due to circadian circuitry, i.e., DN1-inhibition of E cell activity. Temporal synchronization between the DN1 clock and E cell clock likely played an important part in properly generating mid-day siesta (FIG. 13). It might also reflect coordination between the timing of neurotransmitter release and E cell receptivity. As mGluRA mRNA cycled within E cells and peaked around noon, and Vglut mRNA cycled similarly within DN1s, either or both molecules could contribute to the timing of inhibition (FIG. 8A). The RNAi results indeed indicate that both molecules contribute to modulation of the siesta and the E peak (FIGS. 8B and 8C).

Previous studies from two different groups emphasized the role of DN1s in maintaining DD rhythmicity, e.g., as a bridge between the M cells and DH44-containing PI neurons to control DD rhythmicity. However, there is no evidence that flies with silenced or ablated DN1s have compromised DD rhythmicity. Indeed, flies without neurotransmitter output from DN1s are still rhythmic (FIG. 12), which may also indicate that morning activity can be rather unimportant to DD rhythmicity. (Note that females with essentially no morning activity were still rhythmic.) Although the neuropeptide DH31 is highly expressed in DN1s and modestly promoted locomotor activity in the late night-early morning, its absence did not affect DD rhythmicity. Lastly, rescuing a PDFR mutant with PDFR expression only in DN1s potently rescued morning activity but rescued DD rhythmicity poorly. This DN1 PDFR rescue as much less effective than rescuing its ligand PDF, suggesting that DN1s are not the key PDFR containing target cells that maintain circadian locomotor activity.

Figure 4C:
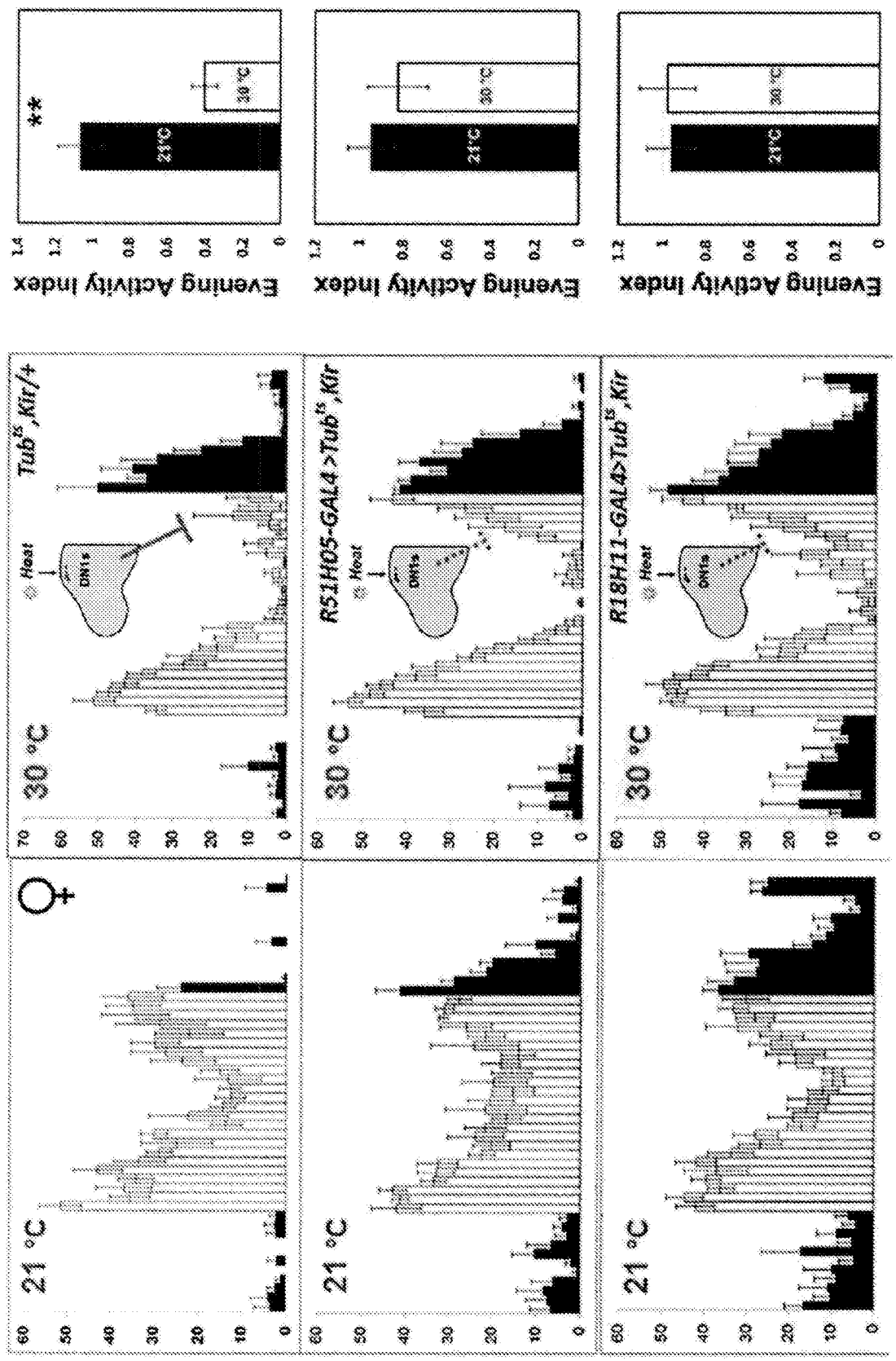
FIG. 4C shows graphs of example activity patterns of control flies (upper panel), compared to activated DN1 (middle panel) and silenced DN1 flies.

Above arguments suggest that the DN1s may principally serve other functions. One group emphasized the wake-promoting effects of DN1s and activated these neurons by using the same PDFR (R18H11)-GAL4 driver line used here (FIG. 4C). Although they showed that this activation inhibited sleep before dawn, a positive effect on the mid-day siesta as well as inhibition of the subsequent E peak as reported here was evident in their data (shown in FIG. 7). Substantially similar results were obtained with another GAL4 line, this one derived from the Vglut regulatory region. This driver also labeled approximately 5 putative glutamatergic DN1s in each hemisphere, an expression pattern that was very similar if not identical to that of the PDFR (R18H11)-GAL4 driver line (data not shown). The 5 cells may be uniform, in which case they all make contact with E cells via glutamate and are also contacted by PDF cells to modulate morning activity. Alternatively, the two interactions may take place on different subpopulations of these 5 DN1s. In either case, there must be time-of-day regulation to determine dominance, i.e., the PDF cell interaction dominates in the late night-early morning whereas the E cell interaction dominates in the mid-day and evening (FIG. 9B).

These two interactions and their temporal coordination are highlighted by the behavioral consequences of DN1 activation at different times of day. As predicted from the literature, activation of DN1s from ZT0-4 promotes locomotor activity whereas activation from ZT7-12 suppresses activity (potentiation of the siesta; FIGS. 6B and 6C). This novel time-of-day activation effect on behavior may be influenced by circadian changes in neuronal contacts, as well as by cycling signaling molecules within DN1s or other circadian neurons (e.g., FIG. 8A). Although similar conclusions resulted from extensive dTrpA1 activation experiments (FIG. 7-8 and data not shown), the fast activation of circadian neuron activity in wake, behaving flies with 627 nm red light avoided issues with temperature manipulations; these were further complicated in the case of DN1s as their activity was temperature-sensitive. The optogenetic approach convincingly demonstrated the different consequences of DN1 activation at different times of day (FIGS. 6B and 6D).

In accordance with aspects of the present disclosure, several important innovations have been described. In particular, use of a 96 well plate assay was described, providing cost-effective way loading and analyzing a large number of small organisms. In addition, it was recognized that a plate assay can be readily adapted to operate with luciferase ("LUC") top counter, providing additional capabilities not possible with prior technologies, such as Trikinetics monitors. In addition, in contrast to Trikenitics monitors, the described recording system is able to achieve uniform illumination for optogenetics using LEDs properly configured therein, which achieving similar performance (FIG. 6A and data not shown).

Another technical innovation includes use of CaLexA-LUC assay, which in some applications can be performed substantially concurrently with video monitoring. As shown herein, the LUC assay indicated that DN1 neuronal activity is sensitive to temperature. This sensitivity may be related to the temperature-sensitive splicing of the period gene, which also positively impacts the siesta. One possibility is that splicing occurs within DN1s and affects neuronal activity. Above-described systems and methods can provide real-time capabilities for manipulating and monitor neuronal activity over days if not weeks. It is envisioned that these capabilities can facilitate the study of many other neuronal circuits and behaviors in wake-behaving flies as well as in other organisms. In some applications, CaLexA-LUC may also be superior as compared to recording neuronal activity using a voltage sensor or calcium reporter in dissected brains. Indeed, initial results suggest substantial differences between in vivo calcium and results from dissected brains (data not shown).

Relevant to the CaLexA-LUC assay is the dramatic sexual dimorphism observed between male and female DN1 activity. Since CaLexA-Luc signal was not specifically calibrated, the differences remain qualitative, in that it is unclear how they translate into calcium levels or firing rates. Nonetheless, the qualitative comparisons can provide useful information. For example, the low DN1 activity of females may be relevant with respect to their relatively weak morning activity. In addition, virgin female DN1 activity was observed to be similar to that of males. As the virgin female siesta was also very similar to that of males, the data suggest that mating dramatically alters DN1 activity.

To address the sexual dimorphism, the sex of DN1 s was swapped using cell-specific expression of UAS-TraF. It is suspected signals from outside the circadian system were involved in suppressing DN1 activity in mated females, perhaps related to octopamine or sex peptide. As such, it is envisioned that future studies might involve identifying this mechanism. Another important area for future study may include the contact of circadian neurons with other parts of the brain as well as the contribution of these connections to other behaviors. The technical advances developed in the course of this work are envisioned to help in determining the functions of these connections.

The present invention has been described in terms of one or more preferred embodiments, and it should be appreciated that many equivalents, alternatives, variations, and modifications, aside from those expressly stated, are possible and within the scope of the invention.

The invention claimed is:
1. A system for monitoring activities of *Drosophila* organisms, the system comprising:
   an organism holder comprising a plurality of chambers configured for holding *Drosophila* organisms therein, the *Drosophila* organisms having a neuron co-expressing a channelrhodopsin and a calcium-dependent transcription activator configured to express luciferase;
   a first activity detector configured to acquire imaging data tracking movements of the *Drosophila* organisms;
   a second activity detector configured to acquire bioluminescence data corresponding to a neural activity of the *Drosophila* organisms;
   an activity control module configured to apply optogenetic stimulation to the *Drosophila* with a light source;
   a light-tight enclosure having a light-tight vent, the light-tight enclosure including the organism holder, the first activity detector, the activity control module, and the second activity detector;
   a processor configured to:
      provide optogenetic stimulation to the neuron using the light source at an intensity and duration sufficient to modify bioluminescence intensity relative to the absence of optogenetic stimulation;
      receive imaging data and bioluminescence data acquired over a time period extendible to a nominal life cycle of the *Drosophila* organisms;

correlate, using the received data, changes in a behavioral activity and the bioluminescence data as a result of the applied optogenetic stimulation of the *Drosophila* organisms;

determine, based on the correlation, an activity profile for the *Drosophila* organisms, the activity profile including information associated with a sleep pattern or a wake pattern of the *Drosophila* organisms;

generate, using the activity profile, a report indicating a relationship between the neuron and the sleep pattern or the wake pattern of the *Drosophila* organism; and an output for displaying the report.

2. The system of claim 1, wherein the plurality of chambers are configured to include a sufficient amount of nourishment for sustaining the *Drosophila* organisms over the time period.

3. The system of claim 1, wherein the time period is extendible to 4 weeks.

4. The system of claim 1, wherein the activity control module further includes one or more of a vibration source, a temperature source, an electrical source, or a combination thereof, configured to apply the stimulation.

5. The system of claim 1, wherein the one or more light source includes a light emitting diode.

6. The system of claim 1, wherein the organism holder comprises multiple chamber units that can be assembled together.

7. The system of claim 1, wherein the organism holder comprises a 96-well plate.

8. The system of claim 1, wherein the calcium-dependent transcription activator configured to express luciferase comprises CaLexA-LUC.

9. The system of claim 1, wherein the channelrhodopsin comprises CsChrimson.

10. A method for controlling activities of *Drosophila* organisms, the method comprising:

acquiring, using a first activity detector, imaging data tracking movements of the *Drosophila* organisms from within an organism holder comprising a plurality of chambers configured for holding the *Drosophila* organisms therein, the *Drosophila* organisms having a neuron co-expressing a channelrhodopsin and a calcium-dependent transcription activator configured to express luciferase;

acquiring, using a second activity detector, bioluminescence data corresponding to a neural activity of the *Drosophila* organisms;

providing, using a light source, optogenetic stimulation to the neuron at an intensity and duration sufficient to modify bioluminescence in the neuron;

correlating, using the acquired data, changes in a behavioral activity and the bioluminescence data as a result of the applied optogenetic stimulation of the *Drosophila* organisms;

determining, using the correlation, an activity profile for the *Drosophila* organisms, the activity profile including information associated with a sleep pattern or a wake pattern of the *Drosophila* organisms; and generating, using the activity profile, a report indicating a relationship between the neuron and the sleep pattern or the wake pattern.

11. The method of claim 10, wherein the method further comprises providing an additional stimulation using one or more of a light source, a temperature source, a vibration source, an electrical source, or a combination thereof.

12. The method of claim 10, wherein the method further comprises generating, using the activity profile, information associated with a circadian cycle of the *Drosophila* organisms.

13. The method of claim 10 wherein the time period is extendible to 4 weeks.

14. A system for monitoring activities of *Drosophila* organisms, the system comprising:

an organism holder comprising a plurality of chambers configured for holding *Drosophila* organisms therein;

a vibration source mechanically coupled to the organism holder, the vibration source configured to induce or transmit vibrations to the organism holder;

a first activity detector configured to acquire imaging data tracking movements of the *Drosophila* organisms;

a second activity detector configured to acquire bioluminescence data corresponding to a neural activity of the *Drosophila* organisms;

a processor configured to:

receive imaging data and bioluminescence data acquired over a time period extendible to a nominal life cycle of the *Drosophila* organisms;

correlate, using the received data, a behavioral activity and a neural activity of the *Drosophila* organisms;

determine, based on the correlation, an activity profile for the *Drosophila* organisms;

generate, using the activity profile, a report indicative of a condition of the *Drosophila* organisms over the time period;

an output for displaying the report, and wherein the organism holder rests on a base, and wherein the vibration source moves the organism holder along a track defined by guides on the base.

15. The system of claim 14, wherein the vibration source is a solenoid.

16. The system of claim 14, wherein the organism holder rests on a base elevated by vibration isolation supports.

* * * * *